United States Patent [19]
Williams et al.

[11] Patent Number: 5,851,821
[45] Date of Patent: Dec. 22, 1998

[54] DNA REPLICATION-REGULATING GENES

[75] Inventors: R. Sanders Williams, Dallas, Tex.;
Bruce Stillman, Cold Spring Harbor, N.Y.

[73] Assignees: Cold Spring Harbor Laboratory, Cold Spring Harbor, N.Y.; The Board of Regents, The University of Texas System, Austin, Tex.

[21] Appl. No.: 643,034

[22] Filed: May 2, 1996

[51] Int. Cl.$^6$ ............................. C12N 15/63; C12N 15/85; C07H 21/04; C07K 14/00

[52] U.S. Cl. ..................... 435/320.1; 536/23.5; 536/23.1; 435/325; 530/350

[58] Field of Search ................................ 536/23.1, 23.5; 435/6, 320.1, 325; 530/350, 387.1

[56] References Cited

FOREIGN PATENT DOCUMENTS

| | | |
|---|---|---|
| 07274971 | 10/1995 | Japan . |
| 93/10242 | 5/1993 | WIPO . |
| 93/23571 | 11/1993 | WIPO . |
| 94/23029 | 10/1994 | WIPO . |
| 95/16694 | 6/1995 | WIPO . |
| 95/21917 | 8/1995 | WIPO . |

OTHER PUBLICATIONS

Bell, S.P., et al., "The Multidomain Strucuture of ORC1p Reveals Similarity to Regulators of DNA Replication and Transcriptional Silencing," *Cell*, 83:563 (1995).

Bruschi, C.V., et al., "The Genomic Instability of Yeast cdc6–1/cdc6–1 Mutants Involves Chromosome Structure and Recombination," *Mol. Gen. Genet.*, 249:8–18 (1996).

Bueno, A. and Russell, P., "Dual Functions of CDC6: a Yeast Protein Required for DNA Replication Also Inhibits Nuclear Division," *EMBO*, 11:2167–2176 (1992).

Cocker, J.H., et al., "An Essential Role for the Cdc6 Protein in Forming the Pre–Replicative Complexes of Budding Yeast," *Nature*, 379:180 (1996).

Gavin, K.A., et al., "Conserved Initiator Proteins in Eukaryotes," *Science*, 270:1667–1671 (1995).

Hartwell, J., "Sequential Function of Gene Products Relative to DNA Synthesis in the Yeast Cell Cycle," *J. Mol. Biol.*, 15:803–817 (1976).

Hogan, E. and Koshland, D., "Addition of Extra Origins of Replication to a Miniochromosome Supresses its Mitotic Loss in cdc6 and cdc14 Mutant of *Saccharomyces cerevisiae*," *PNAS*, 89:3098–3102 (1992).

Jallepalli, P. and Kelly, T., "RumI and Cdc18 Link Inhibition of Cyclin–Dependent Kinases to the Initiation of DNA Replication in S. pombe.," *Genes and Development*, 10:541–552 (1996).

Kelly, T.J., et al., "the Fission Yeast cdc18+ Gene Product Couples S. Phase to START and Mitosis," *Cell*, 74:371–382 (1993).

Kelly, T.J., et al., "Coupling DNA Replication to the Cell Cycle," *Cold Spring Harbor Symp Quant. Biol.*, 58:637–644 (1993).

Leatherwood, J., et al., Interaction of Cdc2 and Cdc18 with a Fission yeast ORC2–Like Protein, *Nature*, 379:360 (1996).

Li, J.J. and Herskowitz, I, "Isolation of ORC6, a Component of the Yeast Origin Recognition Complex by a One–Hybrid System," *Science*, 262:1870–1874 (1993).

Liang, C., et al., "ORC and CdC6P Interact and Determine the Frequency of Initiation of DNA Replication in the Genome," *Cell* 81:667–676 (1995).

Lisziewicz, J. et al., "Cloning and Characterization of the *Saccharomyces Cerevisiae* CDC 6 Gene," *Nucleic Acids Research*, 16:11507–11520 (1988).

Muzi–Falconi, M., et al., "cdc18+ Regulates Initiation of DNA Replication in *Schizosaccharomyces pombe.*," *PNAS*, 93:1566–1570 (1996).

Nishitani, H. and Nurse, P., "p65$^{cdc18}$ Plans a Major Role Controlling the Initiation of DNA Replication in Fission Yeast," *Cell*, 83:397–405 (1995).

Palmer, R.E., et al., "Mitotic Transmission of Artificial Chromosomes in cdc Mutants of the Yeast, *Saccharomyece cerevisiae*," *Genetics*, 125:763–744 (1990).

Piatti, S., et al., "Cdc6 is an Unstable Protein Whose do novo Synthesis in $G_1$ is Important for the Onset of S Phase and for Preventing a 'Reductional' Anaphase in the Budding Yeast *Saccharomyces cerevisiae*," *EMBO*, 1141:3788–3799 (1995).

Zhou, C., et al., "Molecular Cloning of *Saccharomyces cerevisiae* CDC Gene: Isolation, Identification and Sequence Analysis," *J. Biol. Chem.*, 264:9022–9029 (1989).

Zwerschke, W., et al., "The *Saccharomyces cerevisiae* CDC6 Gene is Transcribed at Late Mitosis and Encodes a ATP/GTPase Contolling S Phase Initiation," *J. Biol. Chem.*, 269:23351–23356 (1994).

Williams, R.S. and Stillman, B., "Human and Xenopus Proteins Related To The Yeast CDC6/cdc18+ Regulators of DNA Replication", *Journal of Investigative Medicine 44*(3) :198A (1996).

Williams, R.S. et al., "A human protein related to yeast Cdc6p", *Proc. Natl. Acad. Sci. USA* 94:142–147 (1997).

Coleman, T.R. et al., "The Xenopus Cdc6 Protein Is Essential for the Initiation of a Single Round of DNA Replication in Cell–Free Extracts", *Cell* 87:53–63 (1996).

Marx, J., "How DNA Replication Originates", *Science* 270:1585–1587 (1995).

Lee, C.C. and Caskey, C.T., "cDNA Cloning Using Degenerate Primers", In PCR Protocols: A Guide To Methods and Applications, Innis, M.A. et al., eds. (CA: Academic Press), pp. 46–53 (1990).

Donovan, S. and Diffley, J.F.X., "Replication origins in eukaroytes", *Current Opinion in Genetics & Development 6 (2)*:203–207 (1996).

Basco, R.D. et al., "Negative Regulation of $G_1$ and $G_2$ by S–Phase Cyclins of *Saccharomyces cerevisiae*", *Molecular and Cellular Biology 15*(9) :5030–5042 (1995).

*Primary Examiner*—Lisa B. Arthur
*Attorney, Agent, or Firm*—Hamilton, Brook, Smith & Reynolds, P.C.

[57] ABSTRACT

The invention pertains to novel genes which function in the regulation of DNA replication and/or entry of a cell into mitosis. The invention also pertains to novel proteins encoded by the genes described herein, antibodies which bind the encoded protein, and homologs of the novel genes which function in regulation of DNA replication and/or entry of a cell into mitosis and hybridize to the DNA sequence of the novel genes.

14 Claims, 10 Drawing Sheets

Box 1

| | | | | | | | | |
|---|---|---|---|---|---|---|---|---|
| Kl | orc1 | G | T | P | T | V | G | K | T |
| Sc | orc1 | G | T | P | G | V | G | K | T |
| Hs | orc1 | G | V | P | G | T | G | K | T |
| Sp | orc1 | G | T | P | G | T | G | K | T |
| Sc | cdc6 | G | P | P | G | T | G | K | T |
| Sp | cdc18 | G | A | P | G | T | G | K | T |

```
Forward Primer:   5'-   GGIGCCCCCGGIACCGGIAAAACC -3'
                           C A    A    A     G   A
                             T    T    T         T
```

Box 3

| | | | | | | | | |
|---|---|---|---|---|---|---|---|---|
| Kl | orc1 | V | V | L | L | D | E | L | D |
| Sc | orc1 | V | V | L | L | D | E | L | D |
| Hs | orc1 | V | L | L | V | D | E | L | D |
| Sp | orc1 | V | V | L | M | D | E | L | D |
| Sc | cdc6 | V | V | V | L | D | E | M | D |
| Sp | cdc18 | I | I | V | L | D | E | M | D |

```
Forward Primer:   5'-   ATCGTGCTCGACGAGATGG -3'
                          G T C G T  A
                              T
```

Box 4

| | | | | | | | | |
|---|---|---|---|---|---|---|---|---|
| Kl | ocr1 | L | D | L | P | E | R | H | L |
| Sc | orc1 | M | D | L | P | E | R | H | L |
| Hs | orc1 | M | D | L | P | E | R | I | M |
| Sp | orc1 | M | D | L | P | E | R | I | L |
| Sc | cdc6 | L | D | M | K | D | R | F | L |
| Sp | cdc18 | L | D | M | T | D | R | F | L |

```
Reverse Primer:   5' -   AGAAAICGGTCIGTCATGTC -3'
                              G    TA T    A
```

```
            10            20            30            40            50            60            70
123 456 789 012 345 678 901 234 567 890 123 456 789 012 345 678 901 234 567 890 123 456 789 012 345 gag cgc ggc tgg agt ttg ctg ccg ctg tgc agt ttg ttc agg ggc ttg tgg cgg tga gtc cga gag gct gcg      75 tgt gag aga cgt gag aag gat cct gca ctg agg agg tgg aaa gaa gat tgc tcg agg cct ggg gtc tgt         150 gag aca gcg gag ctg ggt gaa ggc tgc cgg ttc cga ggc ctg agc tgt gct gtc ATG CCT CAA ACC CGA         225
                                                                        Met Pro Gln Thr Arg TCC CAG GCA CAG GCT ACA ATC AGT TTT CCA AAA AGG AAG CTG TCT CGG GCA TTG AAC AAA GCT AAA AAC TCC AGT 300
Ser Gln Ala Gln Ala Thr Ile Ser Phe Pro Lys Arg Lys Leu Ser Arg Ala Leu Asn Lys Ala Lys Asn Ser Ser GAT GCC AAA CTA GAA CCA ACA AAT GTC CAA ACC TGT GTA CCT CGT TCT CCT GTA AAA GCC CTG CCT CTC AGC CCC 375
Asp Ala Lys Leu Glu Pro Thr Asn Val Gln Thr Cys Val Pro Arg Ser Pro Val Lys Ala Leu Pro Leu Ser Pro AGG AAA CGT CTG GGC GAT GAC CTA TGC AAC ACT CCC CAT TTA CCT CCT TGT TCT CCA CCA AAG CAA GGC AAG     450
Arg Lys Arg Leu Gly Asp Asp Leu Cys Asn Thr Pro His Leu Pro Pro Cys Ser Pro Pro Lys Gln Gly Lys AAA GAG AAT GGT CCC CCT CAC TCA CAT ACA CTT AAG GGA CGA TTG GTA TTT GAC AAT CAG CTG ACA ATT AAG     525
Lys Glu Asn Gly Pro Pro His Ser His Thr Leu Lys Gly Arg Leu Val Phe Asp Asn Gln Leu Thr Ile Lys TCT CCT AGC AAA AGA GAA CTA GCC GTC GTC CAA AAC ATA CTT TCT TCA GTT CAA AGT CAA GAG ATC             600
Ser Pro Ser Lys Arg Glu Leu Ala Lys Val His Gln Asn Ile Leu Ser Ser Val Arg Lys Ser Gln Glu Ile ACA ACA AAT TCT GAG CAG AGA TGT CCA AAG CTG CTG AAC ACA GAA TCT GCA TGT CCA GAT CGG CCT GCC AGG GAA CAA AGG GAG ATG GAT 675
Thr Thr Asn Ser Glu Gln Arg Cys Pro Lys Leu Leu Asn Thr Glu Ser Ala Cys Val Arg Leu Pro Ala Arg Glu Gln Arg Glu Met Asp TGC TAC CAG CAA AAT TTC TTG AGG GAA CAC ATC TGT GGG AAA GCT GGA AGC CTT TAC CTT TCT GGT GCT CCT GGA 750
Cys Tyr Gln Gln Asn Phe Leu Arg Glu His Ile Cys Gly Lys Ala Gly Ser Leu Tyr Leu Ser Gly Ala Pro Gly GTC ATC AGG AAT ACT GCC CGG ATT CAC AGC CTG CAA GAC CTC AAG GAA CTG AAA AGG TTT AAA ACT ATC ATG     825
Val Ile Arg Asn Phe Ala Arg Ile His Ser Leu Gln Asp Leu Lys Glu Leu Lys Arg Phe Lys Thr Ile Met ACT GGA AAA ACT GCC TGC TTA AGC CGG TTA CAA CTG CAA GAC ATT CTG AAG AAG GAA CTG AAA TTT GGC AAA ATC ATG 900
Thr Gly Lys Thr Ala Cys Leu Ser Arg Leu Gln Leu Gln Asp Ile Leu Lys Lys Glu Leu Lys Phe Gly Lys Ile Met
```

CTG AAT TGC ATG TCC TTG AGG ACT GCC CAG GCT GTA TTC CCA GCT ATT GCT CAG GAG ATT TGT CAG GAA GTA      975
Leu Asn Cys Met Ser Leu Arg Thr Ala Gln Ala Val Phe Pro Ala Ile Ala Gln Glu Ile Cys Gln Glu Val

TCC AGG CCA GCT GGG AAG GAC ATG ATG AGG AAA TTG GAA AAA CAT ATG ACT GCA GAG AAG GGC CCC ATG ATT GTG 1050
Ser Arg Pro Ala Gly Lys Asp Met Met Arg Lys Leu Glu Lys His Met Thr Ala Glu Lys Gly Pro Met Ile Val

TTG GTA TTG GAC GAG ATG CAA CTG GAC AGC AAA GGC CAG GAT GTA TTG TAC CTA TTT GAA TGG CCA TGG         1125
Leu Val Leu Asp Glu Met Gln Leu Asp Ser Lys Gly Gln Asp Val Leu Tyr Leu Phe Glu Trp Pro Trp

CTA AGC AAT TCT CAC TTG GTG CTG ATT GGT CTG ATT GCT AAT ACC CTG GAT CTC ACA GAT CTA CCT AGG CTT     1200
Leu Ser Asn Ser His Leu Val Leu Ile Gly Leu Ile Ala Asn Thr Leu Asp Leu Thr Asp Leu Pro Arg Leu

CAA GCT AGA GAA AAA TGT AAG CCA CTG TTG AAC TTC CCA CCT TAT ACC AGA ATA CAG ATA GTC ACT ATT TTG     1275
Gln Ala Arg Glu Lys Cys Lys Pro Leu Leu Asn Phe Pro Pro Tyr Thr Arg Ile Gln Ile Val Thr Ile Leu

CAA GAT CGA CTT AAT CAG GTA TCT AGA GAT CAG GTT CAA GCA GCT GCA TTC TGT GCC CGC AAA GTC              1350
Gln Asp Arg Leu Asn Gln Val Ser Arg Asp Gln Val Gln Ala Ala Ala Phe Cys Ala Arg Lys Val

TCT GCT GTT TCA GGA GAT GTT CGC AAA GCA CTG GAT GTT TGC GAT GTT ATT GAA GCT ATT GTA GAG TCA GAT GTC 1425
Ser Ala Val Ser Gly Asp Val Arg Lys Ala Leu Asp Val Cys Asp Val Ile Glu Ala Ile Val Glu Ser Asp Val

AAA AGC CAG ACT ATT CTC AAA CCA CTG TCT GAA TGT AAA TCA CCT TCT GAG CCT CTG ATT CCC AAG AGG GTT GGT 1500
Lys Ser Gln Thr Ile Leu Lys Pro Leu Ser Glu Cys Lys Ser Pro Ser Glu Pro Leu Ile Pro Lys Arg Val Gly

CTT ATT CAC TCC ATA GTC CAA GTT GAT ATC TCA GAA GTT AAC AGG ATG GGA CAA GAG GGA GCA CAA GAT         1575
Leu Ile His Ser Ile Val Gln Val Asp Ile Ser Glu Val Asn Arg Met Thr Leu Ser Gln Glu Gly Ala Gln Asp

TCC TTC CCT CTT CAG CAG CAG AAG ATC ATT TTG GTT TGC TCT TTG ATG CTC TTG ATC AGG CAG CAG TTG AAA ATC AAA GAG GTC 1650
Ser Phe Pro Leu Gln Gln Gln Lys Ile Ile Leu Val Cys Ser Leu Met Leu Leu Ile Arg Gln Gln Leu Lys Ile Lys Glu Val

ACT CTG GGG AAG TTA TAT GAA GCC TAC AGT GTC AAA CAG CAG GTG GCG GCT GTG GAC CAG TCA GAG              1725
Thr Leu Gly Lys Leu Tyr Glu Ala Tyr Ser Val Lys Cys Arg Lys Gln Gln Val Ala Ala Val Asp Gln Ser Glu
```

TGT TTG TCA CTT TCA GGG CTC TTG GAA GCC AGG GGC ATT TTA GGA TTA AAG AGA AAC AAG GAA ACC CGT TTG ACA    1800
    Cys Leu Ser Leu Ser Gly Leu Leu Glu Ala Arg Gly Ile Leu Gly Leu Lys Arg Asn Lys Glu Thr Arg Leu Thr

AAG GTG TTT TTC AAG ATT GAA GAG AAA GAA ATA GAA CAT GCT CTG AAA GAT AAA GCT TTA ATT GGA AAT ATC TTA    1875
    Lys Val Phe Phe Lys Ile Glu Glu Lys Glu Ile Glu His Ala Leu Lys Asp Lys Ala Leu Ile Gly Asn Ile Leu

GCT ACT GGA TTG CCT TAA att ctt ctc tta cac ccc cga aag tat tca gct ggc att tag aga gct aca gtc        1950
    Ala Thr Gly Leu Pro ttc att tta gtg ctt tac ttc ggg cct gaa aac aaa tat gac ctt ttt tac ttg aag cca atg aat ttt aat        2025 cta tag att ctt taa tat tag cac aga ata ata tct ttg ggt ctt act att ttt acc cat aaa agt gac cag gta    2100 gac cct ttt taa tta cat tca ctt cta ctt gtg tat ctc tag cca atg tgc ttg caa gtg tac aga tct            2175 gtg tag agg aat gtg tgt ata ttt acc tct tcg ttt gct caa aca tga gtg ggt att ttt ttg gtt ttt ttt        2250 gtt gtt gtt ttt gag gcg cgt taa ctg ccc agg ctg gag tgc aat ggc gcg ttc tct gct cac tac                2325 agc acc cgc ttc cca ggt tga agt gat tct ctt gcc tca gcc tcc cga gta gct ggg att aca ggt gcc cac cac    2400 cgc gcc cag cta att ttt taa ttt tta gta gag aca ggg ttt tac cat gtt ggc cag gct ggt ctt gaa ctc ctg    2475 acc ctc aag tga tct gcc cac ctt ggc ctc cct aag tgc tgg gat tat agg cgt gag cca cca tgc tca gcc att    2550 aag gta ttt tgt taa gaa ctt taa gtt tag ggt aag aat gaa aat gat cca gaa aaa tgc aag caa gtc cac        2625 atg gag att tgg agg aca ctg gtt aaa g
```

```
         10        20        30        40        50        60        70
123 456 789 012 345 678 901 234 567 890 123 456 789 012 345 678 901 234 567 890 123 456 789 012 345
ATG CCA AGC ACC AGG TCT CGG TCT CAA AGC TCC ATT CAG TTT CCC AAG ACT AAA AAG ACT TCT CAG ACG CTC GCC AAA   75
Met Pro Ser Thr Arg Ser Arg Ser Gln Ser Ser Ile Gln Phe Pro Lys Thr Lys Lys Thr Ser Gln Thr Leu Ala Lys

GAG GTC TCA CGT GCA AAG AGC AAG AGC TCT GAG ATC TGC GAT GAC TCT TCC CTC GTC TCC CCG CTC CCA CTT CCA AAA GAG   150
Glu Val Ser Arg Ala Lys Ser Lys Ser Ser Glu Ile Cys Asp Asp Ser Ser Leu Val Ser Pro Leu Pro Leu Pro Lys Glu

CTT CCC AGT CTC CCA CGC AAA CGG CTC GGT GAC AAT CGT TGC AAC ATT CCT CCG ACA TTA AGC TGC TCC CCA   225
Leu Pro Ser Leu Pro Arg Lys Arg Leu Gly Asp Asn Arg Cys Asn Ile Pro Pro Thr Leu Ser Cys Ser Pro

CCC AAG CAG TCT CGC AAA GAG ACT CGC GGC CAG CCA ACC CCT AAG GGG CGT TTA CTT TTT GAT GAG AAC CAG   300
Pro Lys Gln Ser Arg Lys Glu Thr Arg Gly Gln Pro Thr Pro Lys Gly Arg Leu Leu Phe Asp Glu Asn Gln

GCT GCA GCG ACA CCA CTA TCC CCC AAG AAC AGG AAC AGT GTG GGG GTC CTA CAG CCT TAT CTG TCC AGA AAG GGG   375
Ala Ala Ala Thr Pro Leu Ser Pro Lys Asn Arg Asn Ser Val Gly Val Leu Gln Pro Tyr Leu Ser Arg Lys Gly

CAA GAG ACC CCC AGC TCT CGT AAG AGG AAC ACG GCT ATA CCA GAG CGC CTG TTG GCT CGT GAG AGT GAG ACT TCC TGC   525
Gln Glu Thr Pro Ser Ser Arg Lys Arg Asn Thr Ala Ile Pro Glu Arg Leu Leu Ala Arg Glu Ser Glu Thr Ser Cys

TAT CAG AAG GCT AAG CAC GCT ATA AAT ACG ATA ILE CCA GAG GGG AAA GCC CTT TAC ATA TCT GGT GCT CCT GGA ACT   600
Tyr Gln Lys Ala Lys His Ala Ile Asn Thr Ala Ile Pro Glu Gly Lys Ala Leu Tyr Ile Ser Gly Ala Pro Gly Thr

ATC AAG ACC TTC CTG ACA AGT CAT TCT GCT GTT AAG CTG CTG CAG GAT GAT CTC AAG CAG TGC AAG ACC GTT TAC ATC   675
Ile Lys Thr Phe Leu Thr Ser His Ser Ala Val Lys Leu Leu Gln Asp Asp Leu Lys Gln Cys Lys Thr Val Tyr Ile

GGC AAA ACT GCG TGC TTG AAT GCG TGC AGC CTG CAG GCA GTG CCG TTT GAG GCT ATA GAA GAA TCT GGG GGC AAA TCT TCA   750
Gly Lys Thr Ala Cys Leu Asn Leu Asn Lys Ser Gln Ala Val Pro Phe Glu Ala Ile Glu Glu Ser Gly Gly Lys Ser Ser

AAC TGC ATG TCA CGC AGC AGT TCC CAG GCA GTG TTG CCG TTT GAG AAG CTG ACT GTG ACT TCA AAG   
Asn Cys Met Ser Arg Ser Ser Ser Gln Ala Val Leu Pro Phe Glu Lys Leu Thr Val Thr Ser Lys

CTG GCC GCC AAA GAT ATT GTA AGG AGT AGG CAG CTG ACT GAG GTG CTG ACG TCA AAG CCA ATC ATC TTG CTG GTG TTG   825
Leu Ala Ala Lys Asp Ile Val Arg Ser Arg Gln Leu Thr Glu Val Leu Thr Ser Lys Pro Ile Ile Leu Leu Val Leu
```

GAT GAG ATG GAT CAG CTG GAC AGC AGA GGA CAG GAT GTC TTG TAC ACC GTG TTT GAG TGG CCT TGG CTT ACA AAT    900
Asp Glu Met Asp Gln Leu Asp Ser Arg Gly Gln Asp Val Leu Tyr Thr Val Phe Glu Trp Pro Trp Leu Thr Asn

TCT AGG ATG GTT TTA ATC GGC ATT GCT AAC GCA TTG GAT TTG ACA GAC CGT ATT TTG CCC AGG CTA CAA GCT CGA    975
Ser Arg Met Val Leu Ile Gly Ile Ala Asn Ala Leu Asp Leu Thr Asp Arg Ile Leu Pro Arg Leu Gln Ala Arg

CGT CCG TGC AGA CCA CAG TTG CTC AAC TTT TCT CCA TAT ACA AAG GAT CAG ATT CTA CAG GAC AGA   1050
Arg Pro Cys Arg Pro Gln Leu Leu Asn Phe Ser Pro Tyr Thr Lys Asp Gln Ile Leu Gln Asp Arg

CTA AAT ACG GTT TCA GGC GAT CAA GTT CTG GAT AAT GCT GCT ATT CAG TTC TGT GCA AGG AAA ATC TCT GCT GTC   1125
Leu Asn Thr Val Ser Gly Asp Gln Val Leu Asp Asn Ala Ala Ile Gln Phe Cys Ala Arg Lys Ile Ser Ala Val

TCT GGA GAT GCT CGA AAG GCG CTA ACT ATC TGC AGG AGA GCT GTT GAA ATT GTC GAA GCG GAT GTC AGG GGC CAG   1200
Ser Gly Asp Ala Arg Lys Ala Leu Thr Ile Cys Arg Arg Ala Val Glu Ile Val Glu Ala Asp Val Arg Gly Gln

ACT GTC CTT AAG CCT CTA ACT GAA TGT GCG TCT CCT TGT CCA TTA AAC CCT GTT CCA AAA AAG GTC   1275
Thr Val Leu Lys Pro Leu Thr Glu Cys Ala Ser Pro Cys Lys Glu Val Pro Leu Asn Pro Val Pro Lys Val

AGC CTT CCA CAC ATC TCT CGT GTC CTG TCG GAT GTG TAT GGG GAC AAG ATG GCA AGC CGT GAG GGT TCA AGC GAG   1350
Ser Leu Pro His Ile Ser Arg Val Leu Ser Asp Val Tyr Gly Asp Lys Met Ala Ser Arg Glu Gly Ser Ser Glu

AGT TTT CCC TTA CAG CAG AAA   1371
Ser Phe Pro Leu Gln Gln Lys
```

DNA REPLICATION-REGULATING GENES

The invention was supported, in whole or in part, by grants RO1-AR40849, RO1-HL54794, P50-HL55988 and PO1-HL06296 from The National Institutes of Health, and PO1-CA13106 from The National Institutes of Health, National Cancer Institute. The Government has certain rights in the invention.

BACKGROUND OF THE INVENTION

Proliferative growth of normal cells requires an orderly progression through a series of distinct steps, a process known as the cell cycle (Alberts et al., *Cell Growth and Division*, Garland Publishing, Inc., New York). Progression through the cell cycle is modulated by nutrient availability, cell size, and growth factors through complex signaling pathways involving phosphorylation cascades and the strictly regulated expression and stability of specific proteins required at each phase of the cell cycle. In addition, the sequence of cell cycle events is rigorously controlled at specific checkpoints to ensure that each discrete stage in the cell cycle has been completed before the next is initiated. Human diseases associated with abnormal cell proliferation result when these rigorous controls on cell cycle progression are perturbed.

A particularly critical step in the cell cycle involves the decision to replicate DNA. In eukaryotic cells, the initiation of DNA replication has been studied most extensively in fungal species; the budding and fission yeast, *Saccharomyces cerevisiae* and *Schizosaccharomyces pombe*, respectively. Less complete data acquired in insects, amphibians and humans suggest, however, that the fundamental mechanisms, and many of the proteins, involved in this process are similar in all eukaryotes (Sherr, *Cell* 79:551–555 (1994); Nigg, *BioEssays* 17:471 (1995)).

DNA replication is initiated from discrete locations within chromosomes by recruitment of an extensive set of proteins collectively termed the replication machinery (Stillman, *J. Biol. Chem.* 269:7047–7050 (1994a); Stillman, *Cell* 78:725–728 (1994b)). This process is best understood at present from studies on the yeast *S. cerevisiae* and *S. pombe* (Diffley, *Current Opinions in Cell Biology* 6:368–372 (1994); Rowley et al., *Biochimica et Biophysica Acta* 1217:239–256 (1994); Stillman (1994a); Stillman (1994b)). Replication origins in *S. cerevisiae* and *S. pombe* consist of specific DNA sequences (replicators) that are bound by nuclear proteins to provide the framework on which the other components of the replication machinery are assembled (Marahrens and Stillman, *Science* 255:817–823 (1992); Dubey et al., *EMBO* 13:3638–3647 (1994); Marahrens and Stillman, *EMBO* 13:3395–3400 (1994); Newlon and Theis, *Current Opinions in Genetics and Development* 3:752–758 (1994); Rao et al., *Mol. Cell Biol.* 14:7643–7651 (1994); Theis and Newlon, *Mol. Cell Biol.* 14:7652–7659 (1994); Clyne and Kelly, *EMBO* 14:6348–6357 (1995); Rao and Stillman, *PNAS* 92:2224–2228 (1995); Rowley et al., *EMBO* 14:2631–2641 (1995); Huang and Kowalski, *Nucleic Acids Research* 24:816–823 (1996)).

In *S. cerevisiae*, a multisubunit complex known as ORC (Origin Recognition Complex) binds to replicator sites within chromosomes (Bell and Stillman, *Nature* 357:128–134 (1992); Diffley and Cocker, *Nature* 357:169 (1992); Bell et al., *Science* 262:1844–1870 (1993); Li and Herskowitz, *Science* 262:1870–1874 (1993); Micklem et al., *Nature* 366:87–89 (1993); Diffley et al., *Cell* 78:303–316 (1994); Bell et al., *Cell* 83:563 (1995); Liang et al., *Cell* 81:667–676 (1995); Loo et al., *Mol. Cell Biol.* 6:741–756 (1995); Rao and Stillman (1995); Rowley et al. (1995)). ORC consists of six essential protein subunits (Palmer et al., *Genetics* 125:763–774 (1990); Bell and Stillman (1992); Bell et al. (1995)), and at least some of them are found in other eukaryotic species (Ehrenhofer-Murray et al., *Science* 270:1671–1674 (1995); Gavin et al., *Science* 270:1667–1671 (1995); Gossen et al., *Science* 270:1674–1677 (1995); Muzi-Falconi and Kelly, *PNAS* 92:12475–12470 (1995); Carpenter et al., *Nature* 379:357 (1996)). Binding of ORC to replicator DNA sequences in vivo can be detected by footprinting techniques and it appears that ORC is bound to the chromosomes throughout the cell cycle, but the pattern of nuclease digestion changes (Diffley and Cocker (1992); Diffley et al. (1994); Rowley et al. (1994); Dahmann et al., *Current Biology* 5:1257 (1995); Diffley, *Yeast* 11:1651–1670 (1995); Cocker et al., *Nature* 379:180 (1996)). This is consistent with the viewpoint that other factors interact with ORC to trigger the initiation of replication at the G1/S boundary.

In budding yeasts this triggering function resides, at least in part, in a protein called Cdc6p (Hartwell, *J. Cell Biol.* 104:803–817 (1976); Lisziewicz et al., *Nucleic Acids Research* 16:11507–11520 (1988); Zhou et al., *J. Biol. Chem.* 264:9022–9029 (1989); Palmer et al., *Genetics* 125:763–774 (1990); Bueno and Russell, *EMBO* 11:2167–2176 (1992); Hogan and Koshland, *PNAS* 89:3098–3102 (1992); Zwerschke et al., *J. Biol. Chem.* 269:23352–23356 (1994); Liang et al. (1995); Piatti et al., *EMBO* 1141:3788–3799 (1995); Bruschi et al., *Mol. Genet.* 249:8–18 (1996); Cocker et al. (1996)). Fission yeasts contain a closely related protein, $cdc18^+$, that appears to have a similar function (Kelly et al., *Cell* 74:371–382 (1993a); Kelly et al., *Cold Spring Harbor Symp Ouant. Biol.* 58:637–644 (1993b); Nishitani and Nurse, *Cell* 83:397–405 (1995); Jallepalli and Kelly, *Genes and Development* 10:541–552 (1996); Leatherwood et al., *Nature* 379:360 (1996); Muzi-Falconi et al., *PNAS* 93:1566–1570 (1996)). Extensive evidence, acquired from genetic and biochemical studies, supports the viewpoint that $Cdc6p/cdc18^+$ proteins have a unique and important role in the initiation of DNA replication.

SUMMARY OF THE INVENTION

The invention relates to novel genes which function in the regulation of DNA replication and/or entry of a cell into mitosis. In a particular embodiment, the genes are derived from vertebrates, including mammalian cells, particularly those derived from Xenopus or human cells. In one embodiment, the genes have a DNA sequence comprising the DNA sequence of SEQ ID NOS: 1 or 3. The present invention also relates to genes which function in the regulation of DNA replication or the entry of a cell into mitosis and which have a nucleotide sequence which hybridizes under conditions of medium stringency to a DNA sequence of SEQ ID NO: 1 or SEQ ID NO: 3.

The invention also pertains to novel polypeptides or proteins encoded by the genes described herein. In a particular embodiment, the polypeptide or protein has the amino acid sequence of SEQ ID NOS: 2 or 4. In another embodiment, the polypeptide or protein is a recombinant human or Xenopus polypeptide or protein. The invention also relates to vectors for expressing the described proteins or polypeptides and to host cells transformed therewith. The invention further pertains to antibodies which bind the proteins and polypeptides described herein. Furthermore, the invention encompasses pharmaceutical compositions comprising the genes and proteins or polypeptides described herein, as well as methods of treating cancers and other diseases utilizing the genes and proteins or polypeptides described herein.

BRIEF DESCRIPTION OF THE DRAWINGS

FIG. 1 illustrates the design of successful oligonucleotide primers(SEQ ID NOS. 6, 7 and 8). Amino acid sequences from ORC1 proteins from *K. lactis* (Kl), *S. cerevisiae* (Sc), human (Hs) and *S. pombe* (Sp) were aligned in the region of three sequence blocks (Boxes 1, 3 and 4) conserved among these proteins, cdc6p and cdc18$^+$.

FIGS. 3A through 3C illustrate the complete cDNA (SEQ ID NO: 1) and amino acid (SEQ ID NO: 2) sequence of the human CSH gene. The putative initiation codon and the first in-frame stop codon are boxed.

FIGS. 4A and 4B illustrate a multiple sequence alignment of human CSH, Xenopus CSH (xhom912) and related proteins from *S. cerevisiae* and *S. pombe*. Amino acid residues that are identical in both vertebrate proteins, or in one or both vertebrate proteins and one or both fungal proteins, are indicated by dark shading, and conservative substitutions are indicated by light shading. Conserved sequence boxes are enclosed. Areas previously known to be conserved among fungal cdc6p and cdc18$^+$ and among fungal and human orc1p are designated Box 1 through Box 6. Other highly conserved regions newly identified are designated as CSH boxes.

FIGS. 6A and 6B illustrate a partial Xenopus CSH cDNA sequence (SEQ ID NO: 3) and amino acid sequence (SEQ ID NO: 4).

DETAILED DESCRIPTION OF THE INVENTION

Figure 2:
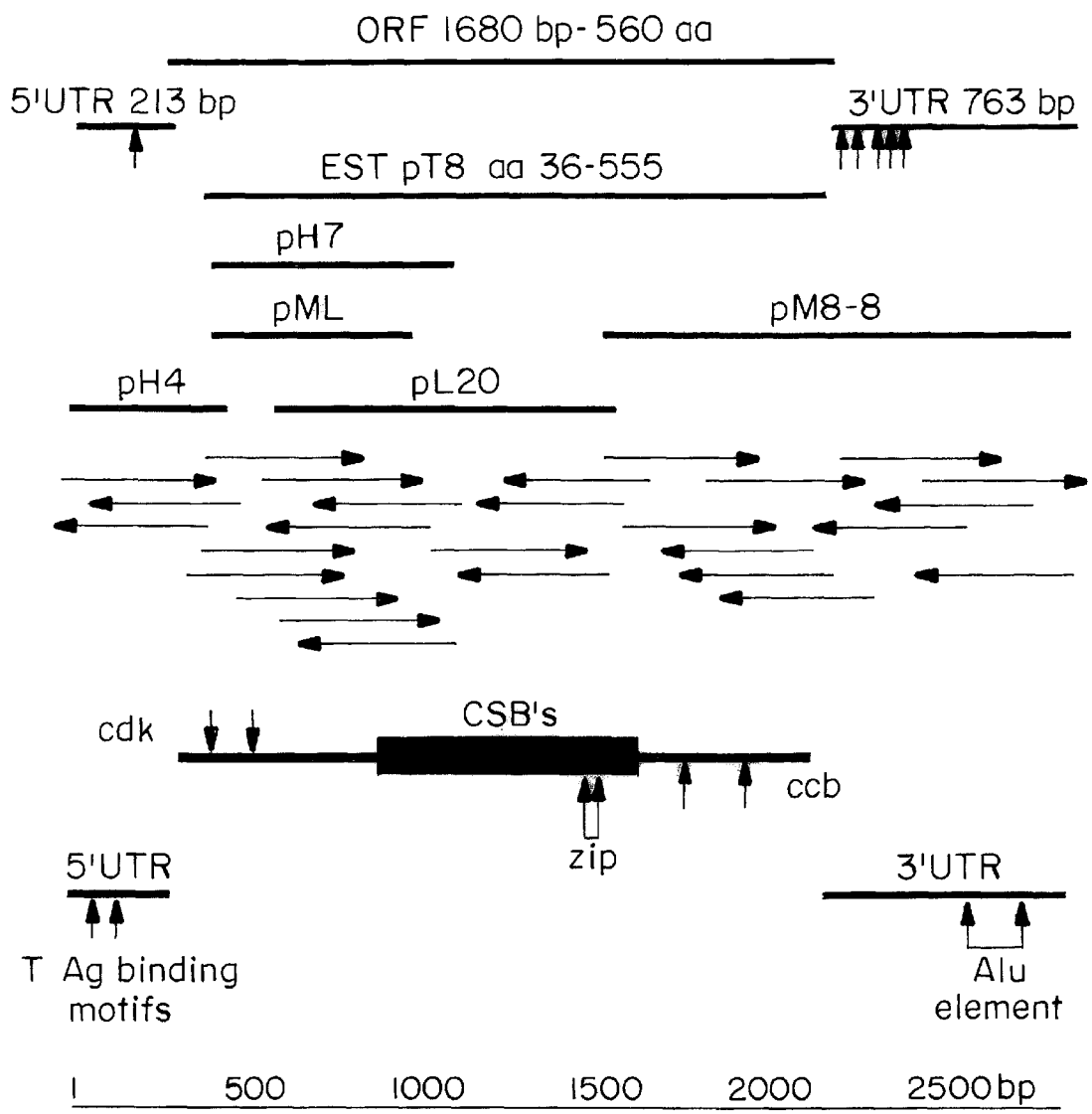
FIG. 2 illustrates the cloning results and sequencing strategy. In-frame stop codons are indicated with dark arrows pointing upwards. Horizontal arrows illustrate the sequencing strategy. Two consensus phosphorylation sites for cyclin-dependent kinases (cdk) are found in the amino terminal region of the protein and are indicated with light arrows pointing downwards. Two consensus sites potentially mediating destruction of the protein at specific stages of the cell cycle (ccb) are present toward the carboxyl terminus and are indicated with light arrows pointing upwards.

The CDC6 gene was cloned by several labs by complementation of a mutation causing a cell-division-cycle specific growth arrest in *S. cerevisiae* (Hartwell (1976); Lisziewicz et al. (1988); Zhou et al. (1989); Bueno and Russell (1992)). The sequence of the largest subunit of ORC, the Orc1p, is highly related to Cdc6p/cdc18$^+$, particularly in and around a putative purine nucleotide binding motif (Bell et al. (1995)). Yeast strains bearing null mutations in CDC6 are nonviable, and strains bearing temperature sensitive mutations in CDC6 suffer growth arrest with partially unreplicated DNA at the restrictive temperature (Lisziewicz et al. (1988); Zhou et al. (1989); Bueno and Russell (1992); Liang et al. (1995)). Even at temperatures permissive for viability, the frequency at which DNA replication is initiated from specific replicators is reduced in strains with CDC6 mutations (Liang et al. (1995); Piatti et al. (1995)). This phenotype can be reversed if multiple replicator sequences are located on the plasmid that is under selection (Hogan and Koshland (1992)).

Interestingly, over-expression of cdc18$^+$ results in repeated rounds of DNA replication in the absence of mitosis, such that cells accumulate concentrations of DNA greater than a 2N DNA content (normal for diploid cells) (Nishitani and Nurse (1995); Jallepalli and Kelly (1996); Leatherwood et al. (1996)). A similar abnormality is a common defect in human cancer cells. In contrast, under-expression of Cdc6p/cdc18$^+$ causes under-replication of the genome and abnormal entry into mitosis (Kelly et al. (1993a) and (1993b); Liang et al. (1995); Piatti et al. (1995); Muzi-Falconi et al. (1996)). The abundance of functional Cdc6p/cdc18$^+$ appears, therefore, to be rate-limiting for initiation of DNA replication at individual replicators.

CDC6 and cdc18$^+$ genes are expressed at specific stages of the cell cycle (Kelly et al. (1993a); Zwerschke et al. (1994); Piatti et al. (1995); Muzi-Falconi et al. (1996)). Expression of mRNA encoding Cdc6p peaks at the end of M phase in rapidly cycling *S. cerevisiae* cells, but a second peak of expression is evident in G1 if G1 is prolonged (Zwerschke et al. (1994); Piatti et al. (1995)). In contrast, the cdc18$^+$ gene is expressed only at the G1 to S phase transition (Kelly et al. (1993a)). Both of these proteins are very unstable: the half life of cdc18$^+$ and Cdc6p has been estimated as 5 minutes or less (piatti et al. (1995); Jallepalli and Kelly (1996); Muzi-Falconi et al. (1996)). Concentrations of cdc18$^+$ peak at the G1/S boundary and decline during late S phase, consistent with a role in triggering DNA replication. A requirement for renewed synthesis of Cdc6p/cdc18$^+$ is an important component of the mechanism that ensures that each segment of chromosomal DNA is replicated once, and only once, in each cell cycle.

Cdc6p and cdc18$^+$ are not only rate limiting for replication initiation, but these proteins have additional regulatory functions in controlling subsequent progression through the cell cycle. A deficiency in functional Cdc6p/cdc18$^+$ causes mitosis in the absence of DNA replication (reductional anaphase) (Kelly et al. (1993a); Piatti et al. (1995)), leading to cell death. Conversely, overexpression of cdc18$^+$ stimulates additional rounds of DNA replication in the absence of mitosis, promoting polyploidy (Nishitani and Nurse (1995)). Thus, a decline in the concentration of Cdc6p/cdc18$^+$ after the initiation of DNA replication appears to be necessary to release checkpoint controls and permit entry into mitosis (Bueno and Russell (1992)). The abundance of cdc18$^+$ is down-regulated by the activity of mitotic cyclins and cyclin-dependent kinase activity, and up-regulated by cyclin-dependent kinase (CDK) inhibitors such as rum1$^+$ protein (Jallepalli and Kelly (1996)).

Cdc6p demonstrates both functional and physical interactions with ORC protein subunits that bind to origins of DNA replication (Li and Herskowitz (1993); Liang et al. (1995)). Concomitant expression of temperature sensitive mutant forms of Cdc6p and either Orc2p or Orc5p is lethal at temperatures permissive for strains bearing only single mutations (synthetic lethality) (Liang et al. (1995)). Conversely, high concentrations of Cdc6p generated from multicopy plasmids can rescue DNA replication at non-permissive temperatures in yeast strains bearing temperature sensitive mutations in the ORC5 gene. Furthermore, Cdc6p is present in protein complexes immunoprecipitated from yeast nuclear protein extracts with monoclonal antibodies directed against ORC subunits (Liang et al. (1995)). It also appears that the *S. pombe* cdc18$^+$ protein may interact with ORC (Leatherwood et al. (1996)). Evidence suggests that the Cdc6p protein may be an ATPase (Zweschke et al. (1994)). The putative purine nucleotide binding motif in the Cdc6p is essential for viability in yeast (M. Weinreich and B. Stillman, unpublished data). In concert, these data establish an important role for Cdc6p/cdc18+ in the initiation of DNA replication and in the progression of cells into mitosis when DNA replication is complete.

As described herein, gene sequences that encode novel proteins closely related to proteins known to control DNA replication and entry into mitosis in fungi have been cloned and characterized. In a particular embodiment, the gene sequence is a human gene sequence (CSH; CDC Six-related protein in Human cells). In another embodiment, the gene sequence is a Xenopus laevis CSH gene sequence. The present invention also relates to the peptides or proteins encoded by the genes described herein.

The amino acid sequences of Cdc6p and cdc18+ were aligned, along with those of human and yeast ORC1 proteins previously described (Bell et al. (1995); Gavin et al. (1995)). ORC1 proteins contain several regions closely related to Cdc6p/cdc18+, including a putative nucleotide binding/ATPase domain, but are otherwise dissimilar (Gavin et al. (1995)). Certain regions that are conserved between the Cdc6p and cdc18+ proteins are not present in any of the Orc1 proteins. Based on these sequences, six degenerate oligonucleotide primers for the polymerase chain reaction (PCR) were designed, using blocks of 6 or 7 amino acids that were identical, or nearly so, in Cdc6p and cdc18+, but differed in two or more codons from sequences conserved among ORC1 proteins from H. sapiens, K. lactis, S. pombe and S. cerevisiae. This was important to avoid re-isolation of human ORC1 cDNA. The nucleotide sequence of each oligonucleotide primer was biased to reflect human usage codon probabilities. The design of primers (SEQ ID NOS. 6, 7 and 8) that proved successful in amplifying partial cDNA sequences encoding CSH proteins from both Xenopus and human cDNAs is shown in FIG. 1. The primers were degenerate in the positions shown, and inosine (I) bases were included at positions of highest degeneracy in the predicted nucleotide sequence.

All six primers were tested in all possible combinations in polymerase chain reactions using cDNA prepared from human, amphibian or insect cells as the template. Amphibian and insect embryo mRNAs were used to make cDNA for this purpose because it was proposed that the embryo might store large amounts of the CDC6-related mRNA for the rapid rounds of cell division that occurs in these organisms (Alberts et al. (1989)). A wide variety of reaction conditions were tested with a variety of template DNAs. The conditions that proved successful included 67 mM Tris HCl (pH 8.8), 16.6 mM ammonium sulfate, 10% dimethylsulfoxide, 6.7 mM EDTA, 8 mM magnesium chloride, 10 mM β-mercaptoethanol, 50 pmol of each oligonucleotide primer, 10 ng of DNA template, and 1 unit Taq polymerase in a total reaction volume of 25 μl. Conditions for PCR (29 cycles) included denaturation of DNA for 2 minutes (first cycle) or 40 seconds (subsequent cycles) at 94° C., primer annealing at 42° C. for 1 minute, and primer extension for 1 minute (cycles 1–28) or 5 minutes (cycle 29) at 72° C. Amplified products were purified after agarose gel electrophoresis and cloned into a plasmid vector (pCRII; Gahm et al., PNAS USA 88:10267–10271 (1991)). Complementary DNA inserts were sequenced from purified plasmid DNA using dideoxynucleotide chain termination chemistry (Sanger et al., PNAS USA 74:5463–5467 (1977)).

The most abundant PCR product identified from this screen was obtained using cDNA prepared from mRNA isolated from Xenopus oocytes as templates. The amplified product of 378 nucleotides encoded a predicted amino acid sequence with greater similarity to Cdc6p/cdc18+ than to ORC1 proteins. Using the same Xenopus oocyte cDNA as template, additional PCR was performed using 5' and 3' rapid amplification of cDNA ends (RACE) techniques, which yielded additional Xenopus cDNA segments that included all of the segments conserved in the comparison of Cdc6p and cdc18+. The cloned Xenopus cDNA includes the initiation codon, but does not extend to the authentic 3' terminus of the coding sequence.

Based on the sequence of the Xenopus Cdc6p-related protein, new sets of non-degenerate oligonucleotide primers were synthesized using regions conserved between the predicted Xenopus protein, cdc6p and cdc18+. Further rounds of PCR were performed using cDNA reverse transcribed from RNA isolated from human cells as the template. One of these new primers, containing the sequence 5'-CCTCTCAGCCCCAGGAAACG-3' (SEQ ID NO: 5) in combination with degenerate primers from the original set based on Box 1 or Box 3 (FIG. 1) generated amplification products of 459 and 687 nucleotides, respectively. The predicted amino acid sequence encoded within these segments exhibited greater similarity to Cdc6p and cdc18+ than to ORC1 proteins and was greater than 90% identical to the amino acid sequence of the predicted Xenopus protein.

The larger (687 nt) fragment of human CSH cDNA obtained by PCR amplification was radiolabeled and used as the probe for screening a human cDNA library carried in bacteriophage lambda phage gt10. In the first round of screening of 900,000 phage plaques, 18 clones were positive in duplicate lifts. Of these 18, 5 clones were positive in duplicate in a second round of screening. Each of theses 5 clones was isolated following a third round of plaque purification after plating at low density. Phage DNA was purified and characterized by PCR and restriction digests. cDNA inserts were isolated and cloned into a plasmid vector for sequencing. Plasmid clones isolated from the human cDNA library and used to determine the complete nucleotide sequence of CSH are illustrated schematically in FIG. 2.

The human cDNA encoding CSH includes an open reading frame of 1680 nucleotides, encoding a protein of 560 amino acids. The most upstream ATG, representing the putative initiation codon is flanked by an in-frame stop codon in the 5' untranslated region (UTR). The termination codon of this open reading frame is flanked by multiple in-frame stop codons in the 3' UTR, 821 bases of which were included in the largest cDNA clone isolated from the phage library. Five overlapping segments of this cDNA were cloned into plasmid vectors for sequencing (pH7, pML, pH4, pL20 and pM8-8).

In addition, a match to a human expressed sequence tag was identified in the National Center for Biotechnology Information database. The sequenced region identified in the EST database represents only the region corresponding to amino acids 36–165 of CSH. This region does not have sufficient identity to cdc6p or cdc18+ to be identified without the additional sequence data obtained by cloning the partial Xenopus cDNA. Complete sequencing of the human cDNA clone bearing this tag (EST pT83032) and comparison to the sequence determined from the clones isolated directly from human cDNA showed that it represents a partial cDNA encoding amino acids 36–555 of CSH.

Other landmarks identified in the CSH sequence are shown in the lower portion of FIG. 2. The box labeled CSB's indicates the region containing conserved sequence blocks shared with yeast cdc6p and cdc18+ and ORC1 proteins. Two consensus phosphorylation sites for cyclin-dependent kinases (cdk) (Jans et al., JBC 270:17064–17067 (1995)) are found in the amino terminal region of the protein and are indicated with light arrows pointing downwards. Two consensus sites potentially mediating destruction of the protein at specific stages of the cell cycle (ccb) (Amon et al., *Cell* 77:1037–1050 (1994)) are present toward the carboxyl terminus and are indicated with light arrows pointing upwards. A potential leucine zipper (zip) overlaps with conserved sequence block 4. The 5' UTR included two consensus sites for DNA binding of SV40 T antigen (T Ag) (SenGupta and Borowiec, *EMBO* 4 (1994)), and an Alu repeat sequence (Alu element) is found within the 3' UTR.

Figure 4B:
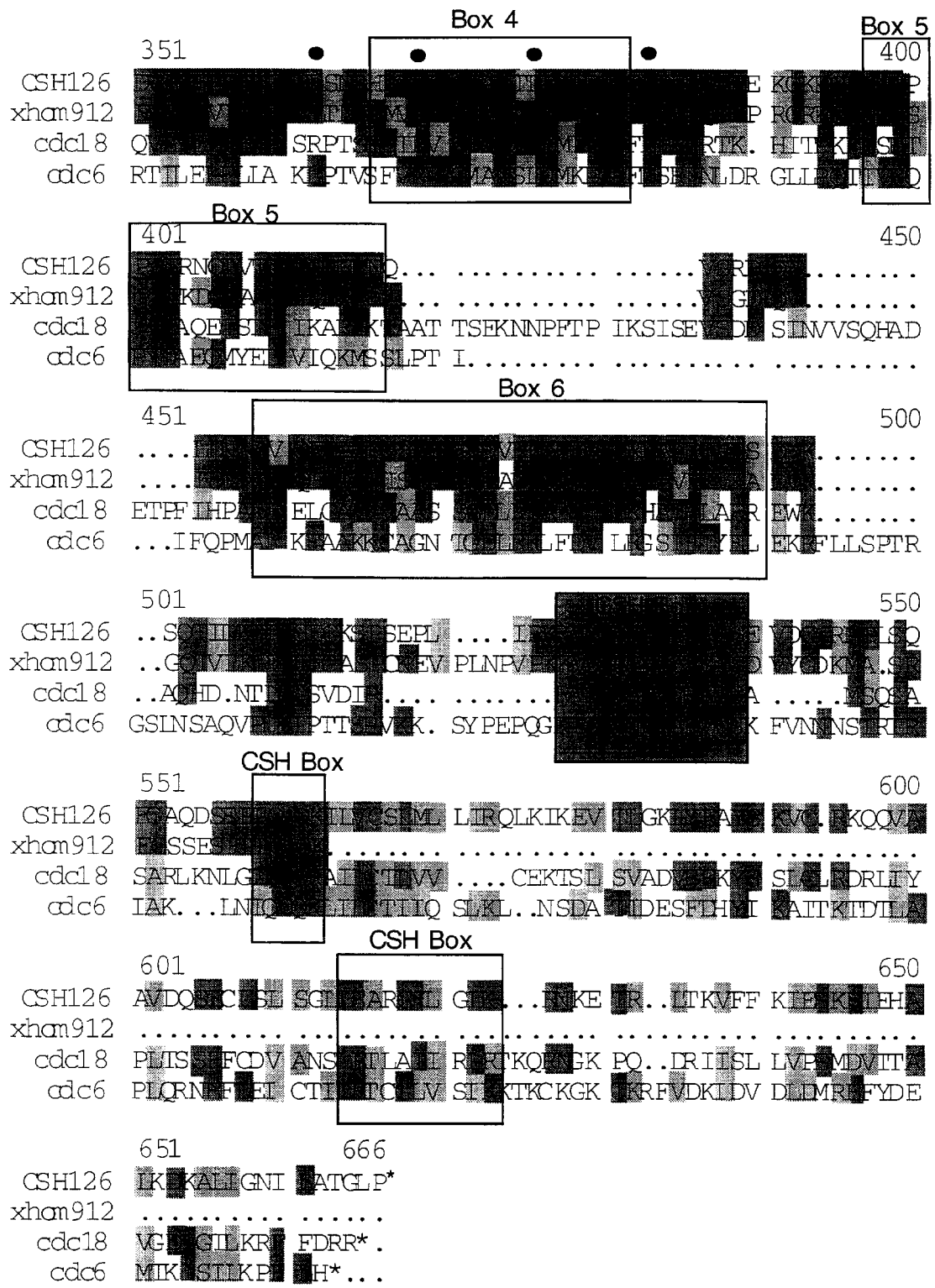

The complete nucleotide sequence of human CSH cDNA is shown in FIGS. 3A and 3B (SEQ ID NO: 1), and the partial nucleotide sequence of Xenopus CSH is shown in FIGS. 6A and 6B (SEQ ID NO: 3). The predicted amino acid sequences are also shown (SEQ ID NOS: 2 and 4, respectively), and the alignment of these amino acid sequences with the fungal Cdc6p/cdc18$^+$ proteins in shown in FIGS. 4A and 4B.

The present invention also relates to genes which function in the regulation of DNA replication or the entry of a cell into mitosis and which have a nucleotide sequence which hybridizes under conditions of medium stringency to a DNA sequence of SEQ ID NO: 1 or SEQ ID NO: 3. Stringency conditions which are appropriately termed "medium stringency" are known to those skilled in the art or can be found in standard texts, such as *Current Protocols in Molecular Biology*, John Wiley & Sons, N.Y. (1989), 6.3.1–6.3.6.

Figure 5:
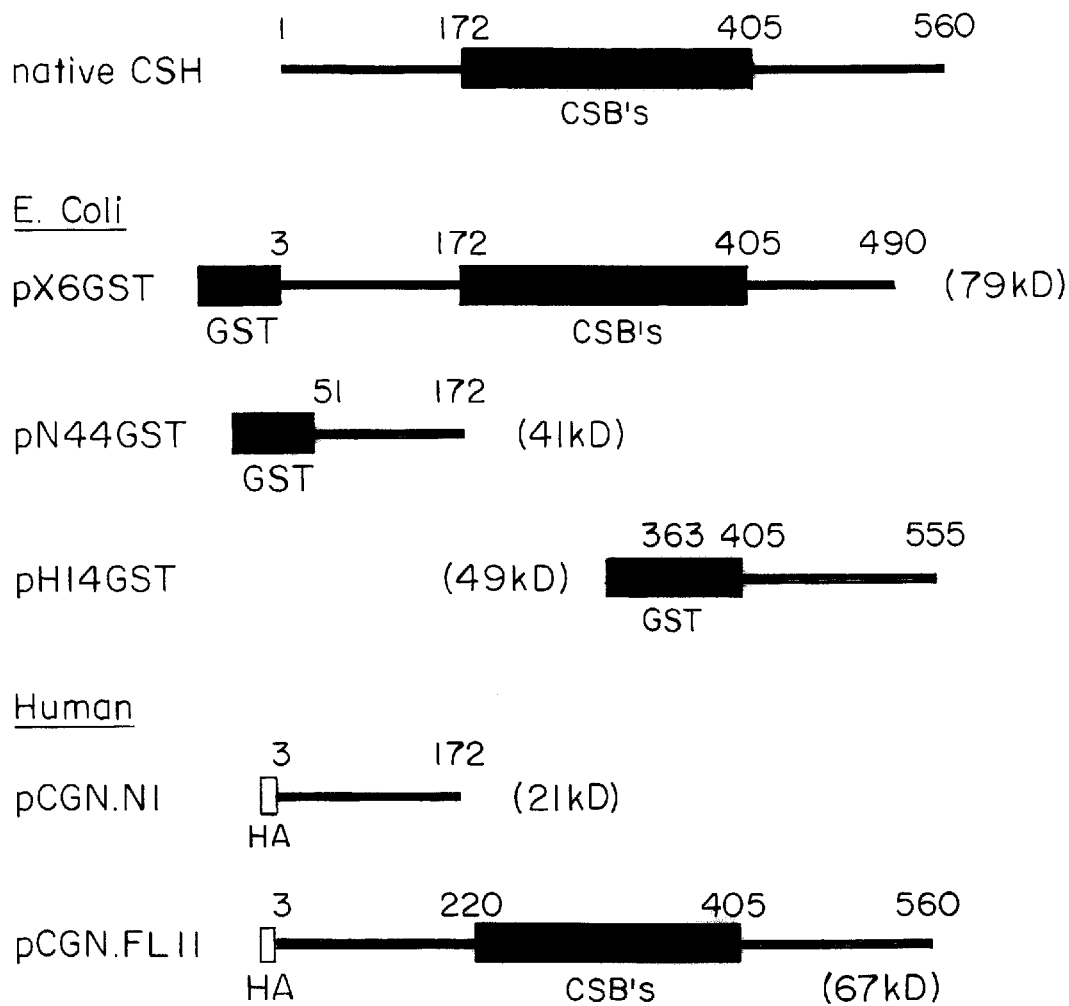
FIG. 5 illustrates plasmid constructions for expression of recombinant CSH in bacteria and in human cells.

Segments of human CSH cDNA were engineered into plasmid vectors for expression of recombinant protein in bacteria and in human cells. The design of these expression plasmids is illustrated schematically in FIG. 5. Portions of human CSH and Xenopus CSH were expressed as GST fusion proteins under the control of the lac Z promoter in *E. coli* and recombinant CSH fusion proteins were purified by binding to glutathione-sepharose beads. Purified recombinant proteins were used to immunize rabbits to generate specific antibodies directed against CSH. These antibodies recognize the recombinant protein expressed in *E. coli*.

The invention also provides additional expression vectors containing a nucleic acid sequence encoding a polypeptide of a CSH gene which is operably linked to at least one regulatory sequence. "Operably linked" is intended to mean that the nucleotide sequence is linked to a regulatory sequence in a manner which allows expression of the nucleic acid sequence. Regulatory sequences are art-recognized and are selected to produce a polypeptide which functions in the regulation of DNA replication and/or entry of the cell into mitosis. Accordingly, the term "regulatory sequence" includes promoters, enhancers, and other expression control elements which are described in Goeddel, *Gene Expression Technology: Methods in Enzymology* 185, Academic Press, San Diego, Calif. (1990). It should be understood that the design of the expression vector may depend on such factors as the choice of the host cell to be transformed and/or the type of protein desired to be expressed. For instance, the polypeptides of the present invention can be produced by ligating the cloned gene, or a portion thereof, into a vector suitable for expression in either prokaryotic cells, eukaryotic cells or both (see, for example, Broach, et al., *Experimental Manipulation of Gene Expression*, ed. M. Inouye (Academic Press, 1983) p. 83; *Molecular Cloning: A Laboratory Manual*, 2nd Ed., ed. Sambrook et al. (Cold Spring Harbor Laboratory Press, 1989) Chapters 16 and 17).

Full-length or partial CSH cDNA sequences were also inserted into a mammalian vector in which expression of recombinant proteins is controlled by the major cytomegalovirus (CMV) immediate early promoter/enhancer and the initiation codon is positioned so as to insert an influenza virus hemagglutinin antigen (HA) tag into the recombinant protein (Tanaka and Herr, *Cell* 60:375–386 (1990)).

Prokaryotic and eukaryotic host cells transfected by the described vectors are also provided by this invention. For instance, cells which can be transfected with the vectors of the present invention include, but are not limited to , bacterial cells such as *E. coli*, insect cells (baculovirus), yeast or mammalian cells such as Chinese hamster ovary cells (CHO).

Thus, a nucleotide sequence derived from the cloning of the CSH peptides and proteins described herein can be used to produce a recombinant form of the protein via microbial or eukaryotic cellular processes. Ligating the polynucleotide sequence into a gene construct, such as an expression vector, and transforming or transfecting into hosts, either eukaryotic (yeast, avian, insect or mammalian) or prokaryotic (bacterial cells), are standard procedures used in producing other well known proteins. Similar procedures, or modifications thereof, can be employed to prepare recombinant proteins according to the present invention by microbial means or tissue-culture technology.

The present invention also relates to antibodies which bind a polypeptide or protein which functions in DNA replication or entry of a cell into mitosis. For instance, polyclonal and monoclonal antibodies which bind to the described polypeptide or protein are within the scope of the invention. A mammal, such as a mouse, hamster or rabbit, can be immunized with an immunogenic form of the polypeptide or protein (i.e., an antigenic fragment of the polypeptide or protein which is capable of eliciting an antibody response). Techniques for conferring immunogenicity on a protein or peptide include conjugation to carriers or other techniques well known in the art. The protein or polypeptide can be administered in the presence of an adjuvant. The progress of immunization can be monitored by detection of antibody titers in plasma or serum. Standard ELISA or other immunoassays can be used with the immunogen as antigen to assess the levels of antibody.

Following immunization, anti-peptide antisera can be obtained, and if desired, polyclonal antibodies can be isolated from the serum. Recombinant CSH protein was generated in bacteria and used to immunize rabbits for production of specific antibodies that recognize epitopes within CSH. Monoclonal antibodies can also be produced by standard techniques which are well known in the art (Kohler and Milstein, *Nature* 256:495–497 (1975); Kozbar et al., *Immunology Today* 4:72 (1983); and Cole et al., *Monoclonal Antibodies and Cancer Therapy*, Alan R. Liss, Inc., pp. 77–96 (1985)).

The CSH genes and peptides or proteins described herein permit the development of new biotechnological and pharmaceutical products to be used for the diagnosis and therapy of human cancers and other diseases associated with abnormal cellular proliferation. For example, the predicted role for CSH in the initiation of DNA replication, particularly the ability to control entry into both S phase and mitosis and to promote polyploidy when over-expressed, suggests that inherited or acquired mutations in the CSH protein, or in transcriptional control regions of the CSH gene that govern its expression, may contribute to the development of human cancers. Diagnostic tests which identify specific disease-related alleles of the CSH gene in peripheral blood lymphocytes or in tumor material will improve the clinical management of patients at risk for the development of specific malignancies or of patients with established malignancies.

Forced expression of yeast proteins related to CSH in fungal cells leads to DNA replication in the absence of mitosis, resulting in polyploidy. The development of polyploidy in human cells often represents a discrete step in the progression of benign or non-aggressive tumors into increasingly malignant forms. Thus, diagnostic tests to identify quantitative or qualitative abnormalities in CSH will aid clinicians in defining the prognosis and in tailoring the therapy for human cancer patients.

CSH also has unique potential as a target for drug- or gene-based therapies designed to slow the growth or promote destruction of human tumor cells. The knowledge of the amino acid sequence of CSH proteins permits the identification of drugs that inhibit the function of CSH, thereby blocking DNA replication and stopping the growth of human tumors. Inhibition of CSH would also drive cells with unreplicated DNA into mitosis, thereby causing cell death. Thus mechanism of action is unique and unlike that of drugs currently used ot treat human cancers. Inhibitors of CSH function will block DNA replication at a step downstream of pathways triggered by growth factors, kinase cascades and proteins acting to regulate the cell cycle.

In addition, drugs or gene therapies that stabilize CSH or augment its function in the G2 and M phases of the cell cycle will block mitosis, even though DNA replication continues. Programmed cell death is a likely consequence of a CSH-induced block to mitosis, which should inhibit tumor growth or promote tumor regression. Thus, drugs or gene-based therapies designed either to block the function of CSH or to augment its function have application to the therapy of human cancers.

In this context, drugs designed on the basis of the CSH protein sequence and intended for use in humans include small non-peptide molecules, peptides or proteins related to CSH or designed to alter the function of endogenous CSH, or DNA sequences encoding proteins or peptides related to CSH or designed to alter the function of endogenous CSH.

In a similar manner, knowledge of the CSH gene sequence can be used to develop novel products to block cell proliferation in disorders other than cancer, including but not limited to atherosclerotic vascular disease, vascular restenosis following medical or surgical reperfusion procedures, psoriasis, inflammatory arthritis and other inflammatory diseases, autoimmune diseases, and rejection of transplanted organs. In addition, the ability of CSH to initiate DNA replication can be exploited for the development of novel products to enhance cell proliferation for therapy of conditions associated with loss of viable tissue, including but not limited to traumatic injury, myocardial infarction, cardiomyopathy, renal failure, hepatic failure and stroke.

Accordingly, the present invention also pertains to pharmaceutical compositions comprising a polypeptide or protein which functions in the regulation of DNA replication or entry of a cell into mitosis. For instance, polypeptides or proteins of the present invention can be formulated with a physiologically acceptable medium to prepare a pharmaceutical composition. The particular physiological medium may include, but is not limited to, water, buffered saline, polyols (e.g., glycerol, propylene glycol, liquid polyethylene glycol) and dextrose solutions. The optimum concentration of the active ingredient(s) in the chosen medium can be determined empirically, according to procedures well known to medicinal chemists, and will depend on the ultimate pharmaceutical formulation desired. Methods of introduction of exogenous polypeptides at the site of treatment include, but are not limited to, intradermal, intramuscular, intraperitoneal, intravenous, subcutaneous, oral and intranasal. Other suitable methods of introduction can also include rechargeable or biodegradable devices and slow release polymeric devices. The pharmaceutical compositions of this invention can also be administered as part of a combinatorial therapy with other agents.

The examples provided herein are offered for the purpose of illustrating the present invention only and are not to be construed to limit the scope of this invention. The teachings of all references cited herein are hereby incorporated herein by reference.

Equivalents

Those skilled in the art will recognize, or be able to ascertain, using no more than routine experimentation, many equivalents to the specific embodiments of the invention described herein. Such equivalents are intended to be encompassed by the following claims:

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 2774 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 219..1898

( x i ) SEQUENCE DESCRIPTION: SEQ ID NO:1:

```
A C C C A C T C G A    G C G C G G C T G G    A G T T T G C T G C    T G C C G C T G T G    C A G T T T G T T C    A G G G G C T T G T                    6 0
```

```
GGCGGTGAGT CCGAGAGGCT GCGTGTGAGA GACGTGAGAA GGATCCTGCA CTGAGGAGGT         120

GGAAAGAAGA GGATTGCTCG AGGAGGCCTG GGTCTGTGA GACAGCGGAG CTGGGTGAAG          180

GCTGCGGGTT CCGGCGAGGC CTGAGCTGTG CTGTCGTC ATG CCT CAA ACC CGA            233
                                           Met Pro Gln Thr Arg
                                            1               5
```

| | | | | | | | | | | | | | | | | |
|---|---|---|---|---|---|---|---|---|---|---|---|---|---|---|---|---|
| TCC | CAG | GCA | CAG | GCT | ACA | ATC | AGT | TTT | CCA | AAA | AGG | AAG | CTG | TCT | CGG | 281 |
| Ser | Gln | Ala | Gln | Ala | Thr | Ile | Ser | Phe | Pro | Lys | Arg | Lys | Leu | Ser | Arg | |
| | | | 10 | | | | | 15 | | | | | 20 | | | |
| GCA | TTG | AAC | AAA | GCT | AAA | AAC | TCC | AGT | GAT | GCC | AAA | CTA | GAA | CCA | ACA | 329 |
| Ala | Leu | Asn | Lys | Ala | Lys | Asn | Ser | Ser | Asp | Ala | Lys | Leu | Glu | Pro | Thr | |
| | | | 25 | | | | | 30 | | | | | 35 | | | |
| AAT | GTC | CAA | ACC | GTA | ACC | TGT | TCT | CCT | CGT | GTA | AAA | GCC | CTG | CCT | CTC | 377 |
| Asn | Val | Gln | Thr | Val | Thr | Cys | Ser | Pro | Arg | Val | Lys | Ala | Leu | Pro | Leu | |
| | | | 40 | | | | | 45 | | | | | 50 | | | |
| AGC | CCC | AGG | AAA | CGT | CTG | GGC | GAT | GAC | AAC | CTA | TGC | AAC | ACT | CCC | CAT | 425 |
| Ser | Pro | Arg | Lys | Arg | Leu | Gly | Asp | Asp | Asn | Leu | Cys | Asn | Thr | Pro | His | |
| | | 55 | | | | | 60 | | | | | 65 | | | | |
| TTA | CCT | CCT | TGT | TCT | CCA | CCA | AAG | CAA | GGC | AAG | AAA | GAG | AAT | GGT | CCC | 473 |
| Leu | Pro | Pro | Cys | Ser | Pro | Pro | Lys | Gln | Gly | Lys | Lys | Glu | Asn | Gly | Pro | |
| 70 | | | | | 75 | | | | | 80 | | | | | 85 | |
| CCT | CAC | TCA | CAT | ACA | CTT | AAG | GGA | CGA | AGA | TTG | GTA | TTT | GAC | AAT | CAG | 521 |
| Pro | His | Ser | His | Thr | Leu | Lys | Gly | Arg | Arg | Leu | Val | Phe | Asp | Asn | Gln | |
| | | | | 90 | | | | | 95 | | | | | 100 | | |
| CTG | ACA | ATT | AAG | TCT | CCT | AGC | AAA | AGA | GAA | CTA | GCC | AAA | GTT | CAC | CAA | 569 |
| Leu | Thr | Ile | Lys | Ser | Pro | Ser | Lys | Arg | Glu | Leu | Ala | Lys | Val | His | Gln | |
| | | | 105 | | | | | 110 | | | | | 115 | | | |
| AAC | AAA | ATA | CTT | TCT | TCA | GTT | AGA | AAA | AGT | CAA | GAG | ATC | ACA | ACA | AAT | 617 |
| Asn | Lys | Ile | Leu | Ser | Ser | Val | Arg | Lys | Ser | Gln | Glu | Ile | Thr | Thr | Asn | |
| | | | 120 | | | | | 125 | | | | | 130 | | | |
| TCT | GAG | CAG | AGA | TGT | CCA | CTG | AAG | AAA | GAA | TCT | GCA | TGT | GTG | AGA | CTA | 665 |
| Ser | Glu | Gln | Arg | Cys | Pro | Leu | Lys | Lys | Glu | Ser | Ala | Cys | Val | Arg | Leu | |
| | | 135 | | | | | 140 | | | | | 145 | | | | |
| TTC | AAG | CAA | GAA | GGC | ACT | TGC | TAC | CAG | CAA | GCA | AAG | CTG | GTC | CTG | AAC | 713 |
| Phe | Lys | Gln | Glu | Gly | Thr | Cys | Tyr | Gln | Gln | Ala | Lys | Leu | Val | Leu | Asn | |
| 150 | | | | | 155 | | | | | 160 | | | | | 165 | |
| ACA | GCT | GTC | CCA | GAT | CGG | CTG | CCT | GCC | AGG | GAA | AGG | GAG | ATG | GAT | GTC | 761 |
| Thr | Ala | Val | Pro | Asp | Arg | Leu | Pro | Ala | Arg | Glu | Arg | Glu | Met | Asp | Val | |
| | | | 170 | | | | | 175 | | | | | 180 | | | |
| ATC | AGG | AAT | TTC | TTG | AGG | GAA | CAC | ATC | TGT | GGG | AAA | AAA | GCT | GGA | AGC | 809 |
| Ile | Arg | Asn | Phe | Leu | Arg | Glu | His | Ile | Cys | Gly | Lys | Lys | Ala | Gly | Ser | |
| | | | 185 | | | | | 190 | | | | | 195 | | | |
| CTT | TAC | CTT | TCT | GGT | GCT | CCT | GGA | ACT | GGA | AAA | ACT | GCC | TGC | TTA | AGC | 857 |
| Leu | Tyr | Leu | Ser | Gly | Ala | Pro | Gly | Thr | Gly | Lys | Thr | Ala | Cys | Leu | Ser | |
| | | | 200 | | | | | 205 | | | | | 210 | | | |
| CGG | ATT | CTG | CAA | GAC | CTC | AAG | AAG | GAA | CTG | AAA | GGC | TTT | AAA | ACT | ATC | 905 |
| Arg | Ile | Leu | Gln | Asp | Leu | Lys | Lys | Glu | Leu | Lys | Gly | Phe | Lys | Thr | Ile | |
| | | 215 | | | | | 220 | | | | | 225 | | | | |
| ATG | CTG | AAT | TGC | ATG | TCC | TTG | AGG | ACT | GCC | CAG | GCT | GTA | TTC | CCA | GCT | 953 |
| Met | Leu | Asn | Cys | Met | Ser | Leu | Arg | Thr | Ala | Gln | Ala | Val | Phe | Pro | Ala | |
| 230 | | | | | 235 | | | | | 240 | | | | | 245 | |
| ATT | GCT | CAG | GAG | ATT | TGT | CAG | GAA | GAG | GTA | TCC | AGG | CCA | GCT | GGG | AAG | 1001 |
| Ile | Ala | Gln | Glu | Ile | Cys | Gln | Glu | Glu | Val | Ser | Arg | Pro | Ala | Gly | Lys | |
| | | | | 250 | | | | | 255 | | | | | 260 | | |
| GAC | ATG | ATG | AGG | AAA | TTG | GAA | AAA | CAT | ATG | ACT | GCA | GAG | AAG | GGC | CCC | 1049 |
| Asp | Met | Met | Arg | Lys | Leu | Glu | Lys | His | Met | Thr | Ala | Glu | Lys | Gly | Pro | |
| | | | 265 | | | | | 270 | | | | | 275 | | | |
| ATG | ATT | GTG | TTG | GTA | TTG | GAC | GAG | ATG | GAT | CAA | CTG | GAC | AGC | AAA | GGC | 1097 |
| Met | Ile | Val | Leu | Val | Leu | Asp | Glu | Met | Asp | Gln | Leu | Asp | Ser | Lys | Gly | |
| | | | 280 | | | | | 285 | | | | | 290 | | | |

```
CAG GAT GTA TTG TAC ACG CTA TTT GAA TGG CCA TGG CTA AGC AAT TCT    1145
Gln Asp Val Leu Tyr Thr Leu Phe Glu Trp Pro Trp Leu Ser Asn Ser
    295             300                 305

CAC TTG GTG CTG ATT GGT ATT GCT AAT ACC CTG GAT CTC ACA GAT AGA    1193
His Leu Val Leu Ile Gly Ile Ala Asn Thr Leu Asp Leu Thr Asp Arg
310             315                 320                 325

ATT CTA CCT AGG CTT CAA GCT AGA GAA AAA TGT AAG CCA CAG CTG TTG    1241
Ile Leu Pro Arg Leu Gln Ala Arg Glu Lys Cys Lys Pro Gln Leu Leu
                330                 335                 340

AAC TTC CCA CCT TAT ACC AGA AAT CAG ATA GTC ACT ATT TTG CAA GAT    1289
Asn Phe Pro Pro Tyr Thr Arg Asn Gln Ile Val Thr Ile Leu Gln Asp
            345                 350                 355

CGA CTT AAT CAG GTA TCT AGA GAT CAG GTT CTG GAC AAT GCT GCA GTT    1337
Arg Leu Asn Gln Val Ser Arg Asp Gln Val Leu Asp Asn Ala Ala Val
        360                 365                 370

CAA TTC TGT GCC CGC AAA GTC TCT GCT GTT TCA GGA GAT GTT CGC AAA    1385
Gln Phe Cys Ala Arg Lys Val Ser Ala Val Ser Gly Asp Val Arg Lys
    375                 380                 385

GCA CTG GAT GTT TGC AGG AGA GCT ATT GAA ATT GTA GAG TCA GAT GTC    1433
Ala Leu Asp Val Cys Arg Arg Ala Ile Glu Ile Val Glu Ser Asp Val
390                 395                 400                 405

AAA AGC CAG ACT ATT CTC AAA CCA CTG TCT GAA TGT AAA TCA CCT TCT    1481
Lys Ser Gln Thr Ile Leu Lys Pro Leu Ser Glu Cys Lys Ser Pro Ser
                410                 415                 420

GAG CCT CTG ATT CCC AAG AGG GTT GGT CTT ATT CAC ATA TCC CAA GTC    1529
Glu Pro Leu Ile Pro Lys Arg Val Gly Leu Ile His Ile Ser Gln Val
            425                 430                 435

ATC TCA GAA GTT GAT GGT AAC AGG ATG ACC TTG AGC CAA GAG GGA GCA    1577
Ile Ser Glu Val Asp Gly Asn Arg Met Thr Leu Ser Gln Glu Gly Ala
        440                 445                 450

CAA GAT TCC TTC CCT CTT CAG CAG AAG ATC TTG GTT TGC TCT TTG ATG    1625
Gln Asp Ser Phe Pro Leu Gln Gln Lys Ile Leu Val Cys Ser Leu Met
    455                 460                 465

CTC TTG ATC AGG CAG TTG AAA ATC AAA GAG GTC ACT CTG GGG AAG TTA    1673
Leu Leu Ile Arg Gln Leu Lys Ile Lys Glu Val Thr Leu Gly Lys Leu
470                 475                 480                 485

TAT GAA GCC TAC AGT AAA GTC TGT CGC AAA CAG CAG GTG GCG GCT GTG    1721
Tyr Glu Ala Tyr Ser Lys Val Cys Arg Lys Gln Gln Val Ala Ala Val
                490                 495                 500

GAC CAG TCA GAG TGT TTG TCA CTT TCA GGG CTC TTG GAA GCC AGG GGC    1769
Asp Gln Ser Glu Cys Leu Ser Leu Ser Gly Leu Leu Glu Ala Arg Gly
            505                 510                 515

ATT TTA GGA TTA AAG AGA AAC AAG GAA ACC CGT TTG ACA AAG GTG TTT    1817
Ile Leu Gly Leu Lys Arg Asn Lys Glu Thr Arg Leu Thr Lys Val Phe
        520                 525                 530

TTC AAG ATT GAA GAG AAA GAA ATA GAA CAT GCT CTG AAA GAT AAA GCT    1865
Phe Lys Ile Glu Glu Lys Glu Ile Glu His Ala Leu Lys Asp Lys Ala
    535                 540                 545

TTA ATT GGA AAT ATC TTA GCT ACT GGA TTG CCT TAAATTCTTC TCTTACACCC   1918
Leu Ile Gly Asn Ile Leu Ala Thr Gly Leu Pro
550                 555                 560

CACCCGAAAG TATTCAGCTG GCATTTAGAG AGCTACAGTC TTCATTTTAG TGCTTTACAC   1978

ATTCGGGCCT GAAAACAAAT ATGACCTTTT TTACTTGAAG CCAATGAATT TTAATCTATA   2038

GATTCTTTAA TATTAGCACA GAATAATATC TTTGGGTCTT ACTATTTTA CCCATAAAAG    2098

TGACCAGGTA GACCCTTTTT AATTACATTC ACTACTTCTA CCACTTGTGT ATCTCTAGCC   2158

AATGTGCTTG CAAGTGTACA GATCTGTGTA GAGGAATGTG TGTATATTTA CCTCTTCGTT   2218

TGCTCAAACA TGAGTGGGTA TTTTTTTGTT TGTTTTTTTT GTTGTTGTTG TTTTTGAGGC   2278
```

-continued

```
GCGTCTCACC CTGTTGCCCA GGCTGGAGTG CAATGGCGCG TTCTCTGCTC ACTACAGCAC    2338

CCGCTTCCCA GGTTGAAGTG ATTCTCTTGC CTCAGCCTCC CGAGTAGCTG GGATTACAGG    2398

TGCCCACCAC CGCGCCCAGC TAATTTTTTA ATTTTTAGTA GAGACAGGGT TTTACCATGT    2458

TGGCCAGGCT GGTCTTGAAC TCCTGACCCT CAAGTGATCT GCCCACCTTG GCCTCCCTAA    2518

GTGCTGGGAT TATAGGCGTG AGCCACCATG CTCAGCCATT AAGGTATTTT GTTAAGAACT    2578

TTAAGTTTAG GGTAAGAAGA ATGAAAATGA TCCAGAAAAA TGCAAGCAAG TCCACATGGA    2638

GATTTGGAGG ACACTGGTTA AAGACCAACC TAATAAATTT CAGCTCGGTG TATTCACGTC    2698

ATAACGAGGA GTGTACGTCT AAAACAGTAG GTGATTACTT AACAGACATC GGTTGACTGA    2758

CAACGAGGTT AAGATG                                                    2774
```

( 2 ) INFORMATION FOR SEQ ID NO:2:

( i ) SEQUENCE CHARACTERISTICS:
        ( A ) LENGTH: 560 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Pro Gln Thr Arg Ser Gln Ala Gln Ala Thr Ile Ser Phe Pro Lys
 1               5                  10                  15

Arg Lys Leu Ser Arg Ala Leu Asn Lys Ala Lys Asn Ser Ser Asp Ala
             20                  25                  30

Lys Leu Glu Pro Thr Asn Val Gln Thr Val Thr Cys Ser Pro Arg Val
             35                  40                  45

Lys Ala Leu Pro Leu Ser Pro Arg Lys Arg Leu Gly Asp Asp Asn Leu
         50                  55                  60

Cys Asn Thr Pro His Leu Pro Pro Cys Ser Pro Pro Lys Gln Gly Lys
 65                  70                  75                  80

Lys Glu Asn Gly Pro Pro His Ser His Thr Leu Lys Gly Arg Arg Leu
                 85                  90                  95

Val Phe Asp Asn Gln Leu Thr Ile Lys Ser Pro Ser Lys Arg Glu Leu
             100                 105                 110

Ala Lys Val His Gln Asn Lys Ile Leu Ser Ser Val Arg Lys Ser Gln
             115                 120                 125

Glu Ile Thr Thr Asn Ser Glu Gln Arg Cys Pro Leu Lys Lys Glu Ser
             130                 135                 140

Ala Cys Val Arg Leu Phe Lys Gln Glu Gly Thr Cys Tyr Gln Gln Ala
145                 150                 155                 160

Lys Leu Val Leu Asn Thr Ala Val Pro Asp Arg Leu Pro Ala Arg Glu
                 165                 170                 175

Arg Glu Met Asp Val Ile Arg Asn Phe Leu Arg Glu His Ile Cys Gly
             180                 185                 190

Lys Lys Ala Gly Ser Leu Tyr Leu Ser Gly Ala Pro Gly Thr Gly Lys
             195                 200                 205

Thr Ala Cys Leu Ser Arg Ile Leu Gln Asp Leu Lys Lys Glu Leu Lys
         210                 215                 220

Gly Phe Lys Thr Ile Met Leu Asn Cys Met Ser Leu Arg Thr Ala Gln
225                 230                 235                 240

Ala Val Phe Pro Ala Ile Ala Gln Glu Ile Cys Gln Glu Val Ser
             245                 250                 255

Arg Pro Ala Gly Lys Asp Met Met Arg Lys Leu Glu Lys His Met Thr
```

-continued

```
                        260                              265                              270
Ala  Glu  Lys  Gly  Pro  Met  Ile  Val  Leu  Val  Leu  Asp  Glu  Met  Asp  Gln
          275                         280                         285

Leu  Asp  Ser  Lys  Gly  Gln  Asp  Val  Leu  Tyr  Thr  Leu  Phe  Glu  Trp  Pro
     290                         295                         300

Trp  Leu  Ser  Asn  Ser  His  Leu  Val  Leu  Ile  Gly  Ile  Ala  Asn  Thr  Leu
305                           310                         315                         320

Asp  Leu  Thr  Asp  Arg  Ile  Leu  Pro  Arg  Leu  Gln  Ala  Arg  Glu  Lys  Cys
                         325                         330                         335

Lys  Pro  Gln  Leu  Leu  Asn  Phe  Pro  Pro  Tyr  Thr  Arg  Asn  Gln  Ile  Val
               340                         345                         350

Thr  Ile  Leu  Gln  Asp  Arg  Leu  Asn  Gln  Val  Ser  Arg  Asp  Gln  Val  Leu
          355                         360                         365

Asp  Asn  Ala  Ala  Val  Gln  Phe  Cys  Ala  Arg  Lys  Val  Ser  Ala  Val  Ser
     370                         375                         380

Gly  Asp  Val  Arg  Lys  Ala  Leu  Asp  Val  Cys  Arg  Arg  Ala  Ile  Glu  Ile
385                           390                         395                         400

Val  Glu  Ser  Asp  Val  Lys  Ser  Gln  Thr  Ile  Leu  Lys  Pro  Leu  Ser  Glu
                    405                         410                         415

Cys  Lys  Ser  Pro  Ser  Glu  Pro  Leu  Ile  Pro  Lys  Arg  Val  Gly  Leu  Ile
               420                         425                         430

His  Ile  Ser  Gln  Val  Ile  Ser  Glu  Val  Asp  Gly  Asn  Arg  Met  Thr  Leu
          435                         440                         445

Ser  Gln  Glu  Gly  Ala  Gln  Asp  Ser  Phe  Pro  Leu  Gln  Gln  Lys  Ile  Leu
     450                         455                         460

Val  Cys  Ser  Leu  Met  Leu  Leu  Ile  Arg  Gln  Leu  Lys  Ile  Lys  Glu  Val
465                      470                         475                         480

Thr  Leu  Gly  Lys  Leu  Tyr  Glu  Ala  Tyr  Ser  Lys  Val  Cys  Arg  Lys  Gln
               485                         490                         495

Gln  Val  Ala  Ala  Val  Asp  Gln  Ser  Glu  Cys  Leu  Ser  Leu  Ser  Gly  Leu
               500                         505                         510

Leu  Glu  Ala  Arg  Gly  Ile  Leu  Gly  Leu  Lys  Arg  Asn  Lys  Glu  Thr  Arg
          515                         520                         525

Leu  Thr  Lys  Val  Phe  Phe  Lys  Ile  Glu  Glu  Lys  Glu  Ile  Glu  His  Ala
     530                         535                         540

Leu  Lys  Asp  Lys  Ala  Leu  Ile  Gly  Asn  Ile  Leu  Ala  Thr  Gly  Leu  Pro
545                      550                         555                         560
```

( 2 ) INFORMATION FOR SEQ ID NO:3:

( i ) SEQUENCE CHARACTERISTICS:
        ( A ) LENGTH: 1371 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..1368

( x i ) SEQUENCE DESCRIPTION: SEQ ID NO:3:

```
ATG  CCA  AGC  ACC  AGG  TCT  CGG  TCT  CAA  AGC  TCC  ATT  CAG  TTT  CCC  AAG     48
Met  Pro  Ser  Thr  Arg  Ser  Arg  Ser  Gln  Ser  Ser  Ile  Gln  Phe  Pro  Lys
 1              5                        10                       15

AAA  AAG  ACT  TCT  CAG  ACG  CTC  GCC  AAA  GAG  GTC  TCA  CGT  GCA  AAG  AGC     96
Lys  Lys  Thr  Ser  Gln  Thr  Leu  Ala  Lys  Glu  Val  Ser  Arg  Ala  Lys  Ser
          20                       25                       30
```

```
AAG TCT GAG ATC TGC TCC TCT GTC TCC CTC CCG CTC TCT CCA CTT CCC    144
Lys Ser Glu Ile Cys Ser Ser Val Ser Leu Pro Leu Ser Pro Leu Pro
        35                  40                  45

AAA GAG CTT CCC CTC AGT CCA CGC AAA CGG CTC GGT GAT GAC AAT CGT    192
Lys Glu Leu Pro Leu Ser Pro Arg Lys Arg Leu Gly Asp Asp Asn Arg
    50                  55                  60

TGC AAC ATT CCT CCG ACA TTA AGC TGC TCC CCA CCC AAG CAG TCT CGC    240
Cys Asn Ile Pro Pro Thr Leu Ser Cys Ser Pro Pro Lys Gln Ser Arg
65                  70                  75                  80

AAA GAG ACT GGC CAG CCA ACC ACC CCT AAG GGG CGC CGT TTA CTT TTT    288
Lys Glu Thr Gly Gln Pro Thr Thr Pro Lys Gly Arg Arg Leu Leu Phe
                85                  90                  95

GAT GAG AAC CAG GCT GCA GCA GCG ACA CCA CTA TCC CCC CTC AAG AAG    336
Asp Glu Asn Gln Ala Ala Ala Ala Thr Pro Leu Ser Pro Leu Lys Lys
            100                 105                 110

CTA CAG GAT CCT TAT CTG CTG TCC CCT GTG AGA AAG GGG CAA GAG ACC    384
Leu Gln Asp Pro Tyr Leu Leu Ser Pro Val Arg Lys Gly Gln Glu Thr
                115                 120                 125

CCA CCC AGC TCT CGT AAG CAA AGG AAC AGT GTG GGG GTC CAG CTA TTT    432
Pro Pro Ser Ser Arg Lys Gln Arg Asn Ser Val Gly Val Gln Leu Phe
130                 135                 140

AAA CAG GAG GGC TCC TGC TAT CAG AAG GCT AAG CAC GCT TTG AAT ACG    480
Lys Gln Glu Gly Ser Cys Tyr Gln Lys Ala Lys His Ala Leu Asn Thr
145                 150                 155                 160

GCT ATA CCA GAG CGC CTG TTG GCT CGT GAG AGT GAG ACT GCA TTT ATC    528
Ala Ile Pro Glu Arg Leu Leu Ala Arg Glu Ser Glu Thr Ala Phe Ile
                165                 170                 175

AAG ACC TTC CTG ACA AGT CAT GTT TCT GCT GGG AAA GCC GGG AGC CTT    576
Lys Thr Phe Leu Thr Ser His Val Ser Ala Gly Lys Ala Gly Ser Leu
                180                 185                 190

TAC ATA TCT GGT GCT CCT GGA ACT GGC AAA ACT GCG TGC TTG AAT AAG    624
Tyr Ile Ser Gly Ala Pro Gly Thr Gly Lys Thr Ala Cys Leu Asn Lys
            195                 200                 205

CTG CTG CAG GAG ACC AAG GAT GAT CTC AAG CAG TGC AAG ACC GTT TAC    672
Leu Leu Gln Glu Thr Lys Asp Asp Leu Lys Gln Cys Lys Thr Val Tyr
    210                 215                 220

ATC AAC TGC ATG TCA TTG CGC AGC TCC CAG GCA GTG TTT CCG GCT ATA    720
Ile Asn Cys Met Ser Leu Arg Ser Ser Gln Ala Val Phe Pro Ala Ile
225                 230                 235                 240

GCT GAA GAA ATC TCT GGG GGC AAA TCT TCA CTG GCC GCC AAA GAT ATT    768
Ala Glu Glu Ile Ser Gly Gly Lys Ser Ser Leu Ala Ala Lys Asp Ile
                245                 250                 255

GTA AGG AGT TTG GAG AAG CTG GTG ACT TCA AAG GGT CCA ATC ATC TTG    816
Val Arg Ser Leu Glu Lys Leu Val Thr Ser Lys Gly Pro Ile Ile Leu
                260                 265                 270

CTG GTG TTG GAT GAG ATG GAT CAG CTG GAC AGC AGA GGA CAG GAT GTC    864
Leu Val Leu Asp Glu Met Asp Gln Leu Asp Ser Arg Gly Gln Asp Val
            275                 280                 285

TTG TAC ACC GTG TTT GAG TGG CCT TGG CTT ACA AAT TCT AGG ATG GTT    912
Leu Tyr Thr Val Phe Glu Trp Pro Trp Leu Thr Asn Ser Arg Met Val
    290                 295                 300

TTA ATC GGC ATT GCT AAC GCA TTG GAT TTG ACA GAC CGT ATT TTG CCC    960
Leu Ile Gly Ile Ala Asn Ala Leu Asp Leu Thr Asp Arg Ile Leu Pro
305                 310                 315                 320

AGG CTA CAA GCT CGA CGT CCG TGC AGA CCA CAG TTG CTC AAC TTT TCT   1008
Arg Leu Gln Ala Arg Arg Pro Cys Arg Pro Gln Leu Leu Asn Phe Ser
                325                 330                 335

CCA TAT ACA AAG GAT CAG ATT GCT ACC ATT CTA CAG GAC AGA CTA AAT   1056
Pro Tyr Thr Lys Asp Gln Ile Ala Thr Ile Leu Gln Asp Arg Leu Asn
                340                 345                 350
```

```
ACG GTT TCA GGC GAT CAA GTT CTG GAT AAT GCT GCT ATT CAG TTC TGT      1104
Thr Val Ser Gly Asp Gln Val Leu Asp Asn Ala Ala Ile Gln Phe Cys
        355                 360                 365

GCA AGG AAA ATC TCT GCT GTC TCT GGA GAT GCT CGA AAG GCG CTA GAT      1152
Ala Arg Lys Ile Ser Ala Val Ser Gly Asp Ala Arg Lys Ala Leu Asp
    370                 375                 380

ATC TGC AGG AGA GCT GTT GAA ATT GTC GAA GCG GAT GTC AGG GGC CAG      1200
Ile Cys Arg Arg Ala Val Glu Ile Val Glu Ala Asp Val Arg Gly Gln
385                 390                 395                 400

ACT GTC CTT AAG CCT CTA ACT GAA TGT GCG TCT CCT TGT AAA GAA GTC      1248
Thr Val Leu Lys Pro Leu Thr Glu Cys Ala Ser Pro Cys Lys Glu Val
            405                 410                 415

CCA TTA AAC CCT GTT CCA AAA AAG GTC AGC CTT CCA CAC ATC TCT CGT      1296
Pro Leu Asn Pro Val Pro Lys Lys Val Ser Leu Pro His Ile Ser Arg
        420                 425                 430

GTC CTG TCG GAT GTG TAT GGG GAC AAG ATG GCA AGC CGT GAG GGT TCA      1344
Val Leu Ser Asp Val Tyr Gly Asp Lys Met Ala Ser Arg Glu Gly Ser
            435                 440                 445

AGC GAG AGT TTT CCC TTA CAG CAG AAA                                  1371
Ser Glu Ser Phe Pro Leu Gln Gln Lys
        450                 455
```

( 2 ) INFORMATION FOR SEQ ID NO:4:

( i ) SEQUENCE CHARACTERISTICS:
        ( A ) LENGTH: 456 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Met Pro Ser Thr Arg Ser Arg Ser Gln Ser Ser Ile Gln Phe Pro Lys
 1               5                  10                  15

Lys Lys Thr Ser Gln Thr Leu Ala Lys Glu Val Ser Arg Ala Lys Ser
                20                  25                  30

Lys Ser Glu Ile Cys Ser Ser Val Ser Leu Pro Leu Ser Pro Leu Pro
            35                  40                  45

Lys Glu Leu Pro Leu Ser Pro Arg Lys Arg Leu Gly Asp Asp Asn Arg
        50                  55                  60

Cys Asn Ile Pro Pro Thr Leu Ser Cys Ser Pro Pro Lys Gln Ser Arg
65                  70                  75                  80

Lys Glu Thr Gly Gln Pro Thr Thr Pro Lys Gly Arg Arg Leu Leu Phe
                85                  90                  95

Asp Glu Asn Gln Ala Ala Ala Ala Thr Pro Leu Ser Pro Leu Lys Lys
            100                 105                 110

Leu Gln Asp Pro Tyr Leu Leu Ser Pro Val Arg Lys Gly Gln Glu Thr
        115                 120                 125

Pro Pro Ser Ser Arg Lys Gln Arg Asn Ser Val Gly Val Gln Leu Phe
    130                 135                 140

Lys Gln Glu Gly Ser Cys Tyr Gln Lys Ala Lys His Ala Leu Asn Thr
145                 150                 155                 160

Ala Ile Pro Glu Arg Leu Leu Ala Arg Glu Ser Glu Thr Ala Phe Ile
                165                 170                 175

Lys Thr Phe Leu Thr Ser His Val Ser Ala Gly Lys Ala Gly Ser Leu
            180                 185                 190

Tyr Ile Ser Gly Ala Pro Gly Thr Gly Lys Thr Ala Cys Leu Asn Lys
        195                 200                 205
```

-continued

| | | | | | | | | | | | | | |
|---|---|---|---|---|---|---|---|---|---|---|---|---|---|
| Leu | Leu | Gln | Glu | Thr | Lys | Asp | Asp | Leu | Lys | Gln | Cys | Lys | Thr | Val | Tyr |
| | 210 | | | | | 215 | | | | 220 | | | | |
| Ile | Asn | Cys | Met | Ser | Leu | Arg | Ser | Ser | Gln | Ala | Val | Phe | Pro | Ala | Ile |
| 225 | | | | | 230 | | | | | 235 | | | | | 240 |
| Ala | Glu | Glu | Ile | Ser | Gly | Gly | Lys | Ser | Leu | Ala | Ala | Lys | Asp | Ile |
| | | | | 245 | | | | 250 | | | | | 255 | |
| Val | Arg | Ser | Leu | Glu | Lys | Leu | Val | Thr | Ser | Lys | Gly | Pro | Ile | Ile | Leu |
| | | | 260 | | | | | 265 | | | | | 270 | | |
| Leu | Val | Leu | Asp | Glu | Met | Asp | Gln | Leu | Asp | Ser | Arg | Gly | Gln | Asp | Val |
| | | 275 | | | | | 280 | | | | | 285 | | | |
| Leu | Tyr | Thr | Val | Phe | Glu | Trp | Pro | Trp | Leu | Thr | Asn | Ser | Arg | Met | Val |
| | 290 | | | | | 295 | | | | | 300 | | | | |
| Leu | Ile | Gly | Ile | Ala | Asn | Ala | Leu | Asp | Leu | Thr | Asp | Arg | Ile | Leu | Pro |
| 305 | | | | | 310 | | | | | 315 | | | | | 320 |
| Arg | Leu | Gln | Ala | Arg | Arg | Pro | Cys | Arg | Pro | Gln | Leu | Leu | Asn | Phe | Ser |
| | | | | 325 | | | | | 330 | | | | | 335 | |
| Pro | Tyr | Thr | Lys | Asp | Gln | Ile | Ala | Thr | Ile | Leu | Gln | Asp | Arg | Leu | Asn |
| | | | 340 | | | | | 345 | | | | | 350 | | |
| Thr | Val | Ser | Gly | Asp | Gln | Val | Leu | Asp | Asn | Ala | Ala | Ile | Gln | Phe | Cys |
| | | 355 | | | | | 360 | | | | | 365 | | | |
| Ala | Arg | Lys | Ile | Ser | Ala | Val | Ser | Gly | Asp | Ala | Arg | Lys | Ala | Leu | Asp |
| | 370 | | | | | 375 | | | | | 380 | | | | |
| Ile | Cys | Arg | Arg | Ala | Val | Glu | Ile | Val | Glu | Ala | Asp | Val | Arg | Gly | Gln |
| 385 | | | | | 390 | | | | | 395 | | | | | 400 |
| Thr | Val | Leu | Lys | Pro | Leu | Thr | Glu | Cys | Ala | Ser | Pro | Cys | Lys | Glu | Val |
| | | | | 405 | | | | | 410 | | | | | 415 | |
| Pro | Leu | Asn | Pro | Val | Pro | Lys | Lys | Val | Ser | Leu | Pro | His | Ile | Ser | Arg |
| | | | 420 | | | | | 425 | | | | | 430 | | |
| Val | Leu | Ser | Asp | Val | Tyr | Gly | Asp | Lys | Met | Ala | Ser | Arg | Glu | Gly | Ser |
| | | 435 | | | | | 440 | | | | | 445 | | | |
| Ser | Glu | Ser | Phe | Pro | Leu | Gln | Gln |
| | 450 | | | | | 455 | |

(2) INFORMATION FOR SEQ ID NO:5:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:5:

CCTCTCAGCC CCAGGAAACG        20

(2) INFORMATION FOR SEQ ID NO:6:

(i) SEQUENCE CHARACTERISTICS:
        (A) LENGTH: 24 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:6:

| | | | | | | | | | | | | | | | |
|---|---|---|---|---|---|---|---|---|---|---|---|---|---|---|---|
| Gly | Gly | Ile | Gly | Cys | Cys | Cys | Cys | Cys | Gly | Gly | Ile | Ala | Cys | Cys | Gly |
| 1 | | | | 5 | | | | | 10 | | | | | 15 | |
| Gly | Ile | Ala | Ala | Ala | Ala | Cys | Cys |
| | | 20 | | | | | |

(2) INFORMATION FOR SEQ ID NO:7:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:7:

```
Ala Thr Cys Gly Thr Gly Cys Thr Cys Gly Ala Cys Gly Ala Gly Ala
 1               5                  10                  15
Thr Gly Gly
```

(2) INFORMATION FOR SEQ ID NO:8:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:8:

```
Ala Gly Ala Ala Ala Ile Cys Gly Gly Thr Cys Ile Gly Thr Cys Ala
 1               5                  10                  15
Thr Gly Thr Cys
             20
```

We claim:

1. An isolated vertebrate CSH gene comprising the DNA sequence of SEQ ID NO: 1.

2. An isolated vertebrate CSH gene comprising the DNA sequence of SEQ ID NO: 3.

3. An isolated protein encoded by the gene of claim 1.

4. An isolated protein encoded by the gene of claim 2.

5. An isolated protein which functions in the regulation of DNA replication comprising the amino acid sequence of SEQ ID NO: 2.

6. An isolated protein which functions in the regulation of DNA replication comprising the amino acid sequence of SEQ ID NO: 4.

7. An isolated antibody which binds to the protein of claim 5.

8. An isolated antibody which binds to the protein of claim 6.

9. Isolated DNA encoding the amino acid sequence of SEQ ID NO: 2.

10. Isolated DNA encoding the amino acid sequence of SEQ ID NO: 4.

11. A DNA construct comprising the isolated DNA of claim 9 operatively linked to a regulatory sequence.

12. A recombinant host cell comprising the isolated DNA of claim 9 operatively linked to a regulatory sequence.

13. A DNA construct comprising the isolated DNA of claim 10 operatively linked to a regulatory sequence.

14. A recombinant host cell comprising the isolated DNA of claim 10 operatively linked to a regulatory sequence.

* * * * *